(12) United States Patent  
McCaffrey et al.

(10) Patent No.: US 11,826,092 B2  
(45) Date of Patent: Nov. 28, 2023

(54) CAVITATION GUIDEWIRE

(71) Applicant: Medtronic Vascular, Inc., Santa Rosa, CA (US)

(72) Inventors: Gerry Oliver McCaffrey, Tuam (IE); Grainne Teresa Carroll, Galway (IE); Risa Tom Egerter, Galway (IE); Aran Murray, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 1024 days.

(21) Appl. No.: 16/661,736

(22) Filed: Oct. 23, 2019

(65) Prior Publication Data

US 2020/0129231 A1 Apr. 30, 2020

Related U.S. Application Data

(60) Provisional application No. 62/750,516, filed on Oct. 25, 2018.

(51) Int. Cl.
*A61M 25/09* (2006.01)
*A61B 18/14* (2006.01)
(Continued)

(52) U.S. Cl.
CPC ......... *A61B 18/1492* (2013.01); *A61M 25/09* (2013.01); *A61B 17/22022* (2013.01);
(Continued)

(58) Field of Classification Search
CPC ........... A61B 2017/22008; A61B 2017/22021; A61B 2017/22025; A61B 2017/22089;
(Continued)

(56) References Cited

U.S. PATENT DOCUMENTS 5,016,808 A 5/1991 Heil, Jr. et al.
5,246,447 A * 9/1993 Rosen .............. A61B 17/22022
601/24
(Continued)

FOREIGN PATENT DOCUMENTS

WO 2018/075924 A1 4/2018

OTHER PUBLICATIONS

U.S. Appl. No. 16/661,561, filed Oct. 23, 2019, naming inventors McCaffrey et al.
(Continued)

*Primary Examiner* — Timothy J Neal
*Assistant Examiner* — Mitchell Brian Hoag
(74) *Attorney, Agent, or Firm* — Shumaker & Sieffert, P.A.

(57) ABSTRACT

A guidewire includes an elongated member and a shaft extending distally from the elongated member, wherein the elongated member and shaft are configured to be navigated through vasculature of a patient. The guidewire further includes a first conductor extending around the shaft to define an outer perimeter of the guidewire and a first electrode adjacent the shaft. The first conductor is configured electrically connect the first electrode to an energy source. The guidewire further includes a second electrode and a second conductor configured to electrically couple the second electrode to the energy source. The first and second electrodes may be configured to deliver an electrical signal to fluid contacting the first and second electrodes to cause the fluid to undergo cavitation to generate a pressure pulse wave within the fluid.

28 Claims, 13 Drawing Sheets

(51) Int. Cl.
*A61B 18/00* (2006.01)
*A61M 25/00* (2006.01)
*A61B 17/22* (2006.01)

(52) U.S. Cl.
CPC .............. *A61B 2017/22007* (2013.01); *A61B 2017/22038* (2013.01); *A61B 2017/22042* (2013.01); *A61B 2018/00071* (2013.01); *A61B 2018/00345* (2013.01); *A61M 2025/0003* (2013.01)

(58) Field of Classification Search
CPC ........... A61B 2017/22038; A61B 2017/22042; A61B 17/22022; A61B 2018/00071; A61B 2017/22007; A61B 2018/0071; A61M 25/09
See application file for complete search history.

(56) References Cited

U.S. PATENT DOCUMENTS

| | | | | |
|---|---|---|---|---|
| 6,088,610 | A * | 7/2000 | Littmann | A61B 17/12022 600/381 |
| 8,197,463 | B2 | 6/2012 | Intoccia | |
| 8,244,378 | B2 | 8/2012 | Bly et al. | |
| 8,540,729 | B2 | 9/2013 | Teague et al. | |
| 8,600,472 | B2 | 12/2013 | Govari et al. | |
| 9,192,435 | B2 | 11/2015 | Jenson | |
| 9,351,790 | B2 | 5/2016 | Zemel et al. | |
| 9,452,017 | B2 | 9/2016 | Chang et al. | |
| 9,642,673 | B2 | 5/2017 | Adams et al. | |
| 9,717,513 | B2 | 9/2017 | Golan | |
| 9,814,476 | B2 | 11/2017 | Adams et al. | |
| 10,709,490 | B2 * | 7/2020 | Turovskiy | A61B 18/1492 |
| 10,966,737 | B2 * | 4/2021 | Nguyen | A61B 17/2202 |
| 11,020,135 | B1 * | 6/2021 | Hawkins | A61M 25/104 |
| 11,266,425 | B2 | 3/2022 | McCaffrey et al. | |
| 2007/0066978 | A1 * | 3/2007 | Schafer | B06B 1/0253 606/128 |
| 2007/0250143 | A1 | 10/2007 | Sommer | |
| 2009/0099555 | A1 * | 4/2009 | Viohl | A61B 1/00114 606/1 |
| 2009/0248012 | A1 * | 10/2009 | Maor | A61M 5/14 606/41 |
| 2010/0023088 | A1 | 1/2010 | Stack et al. | |
| 2011/0306851 | A1 * | 12/2011 | Wang | A61B 5/02444 606/41 |
| 2014/0005576 | A1 | 1/2014 | Adams et al. | |
| 2014/0031661 | A1 | 1/2014 | Clark et al. | |
| 2014/0046229 | A1 | 2/2014 | Hawkins et al. | |
| 2014/0066915 | A1 * | 3/2014 | Zhou | A61B 18/18 606/41 |
| 2014/0243809 | A1 | 8/2014 | Gelfand et al. | |
| 2015/0018817 | A1 * | 1/2015 | Willard | B29C 48/10 264/129 |
| 2015/0039002 | A1 | 2/2015 | Hawkins | |
| 2015/0320432 | A1 * | 11/2015 | Adams | A61B 17/22012 606/128 |
| 2016/0135828 | A1 | 5/2016 | Hawkins et al. | |
| 2017/0135709 | A1 * | 5/2017 | Nguyen | A61B 17/22022 |
| 2017/0258523 | A1 | 9/2017 | Adams et al. | |
| 2017/0303946 | A1 | 10/2017 | Ku et al. | |
| 2018/0098779 | A1 * | 4/2018 | Betelia | A61B 17/22004 |
| 2018/0153568 | A1 | 6/2018 | Kuoy | |
| 2018/0256250 | A1 * | 9/2018 | Adams | A61B 17/22022 |
| 2018/0304040 | A1 * | 10/2018 | Jalgaonkar | A61M 25/0051 |
| 2019/0150960 | A1 * | 5/2019 | Nguyen | A61B 18/1492 |
| 2019/0262069 | A1 * | 8/2019 | Taff | A61B 18/00 |
| 2019/0381223 | A1 * | 12/2019 | Culbert | A61M 1/77 |
| 2020/0205845 | A1 * | 7/2020 | Yang | A61M 25/0108 |

OTHER PUBLICATIONS

Extended European Search Report from counterpart European Application No. 19205271.0, dated Apr. 2, 2020, 9 pp.

* cited by examiner

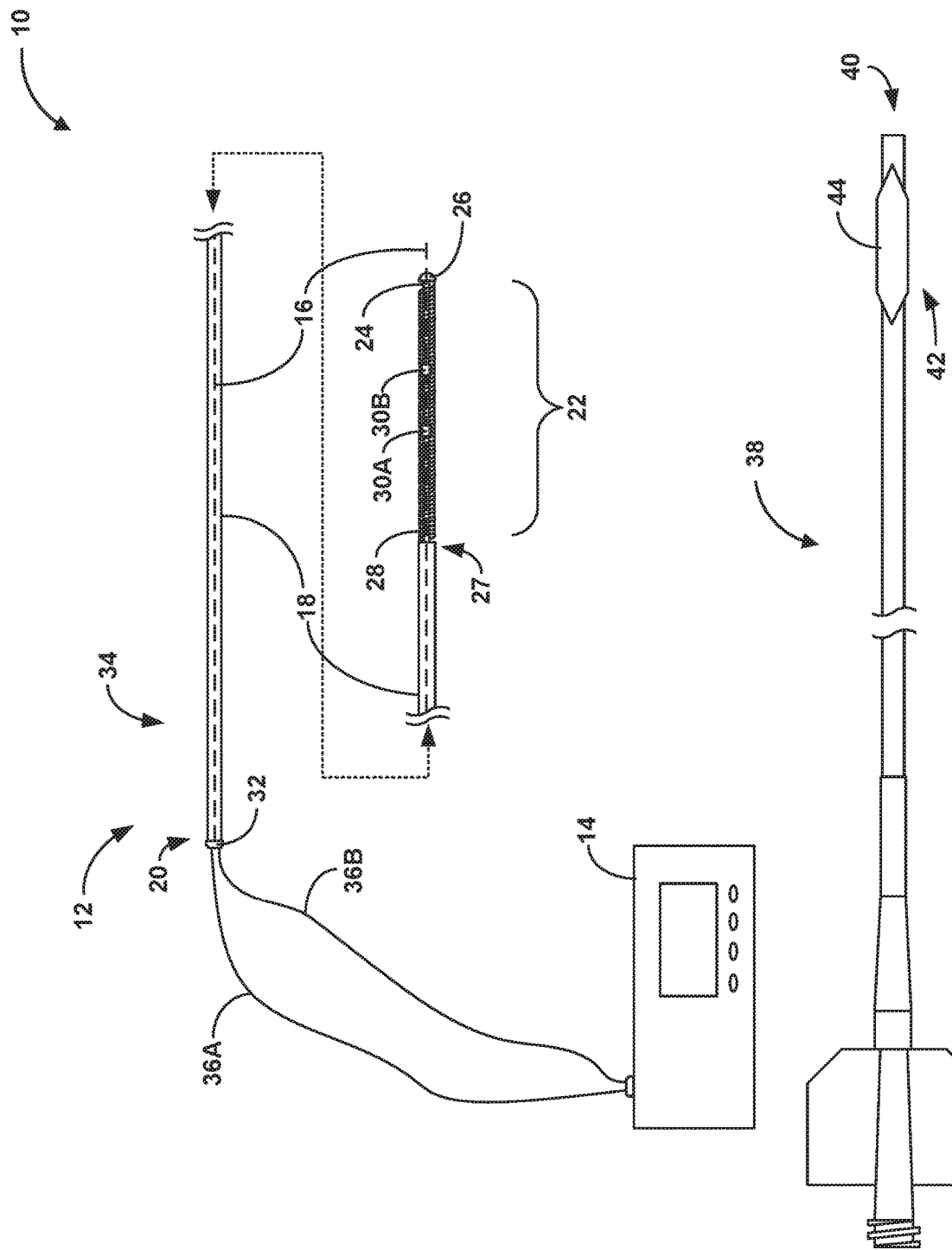

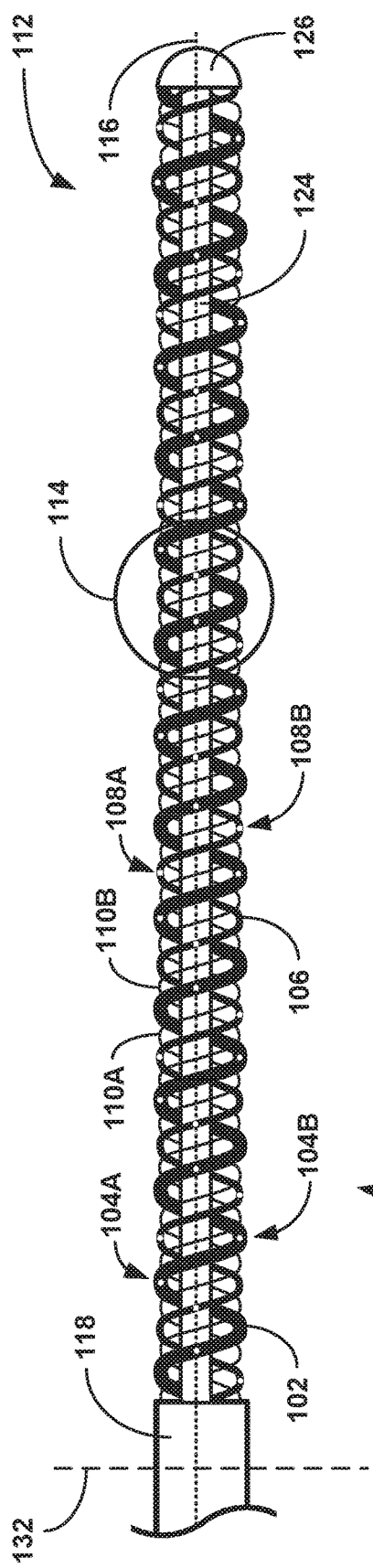
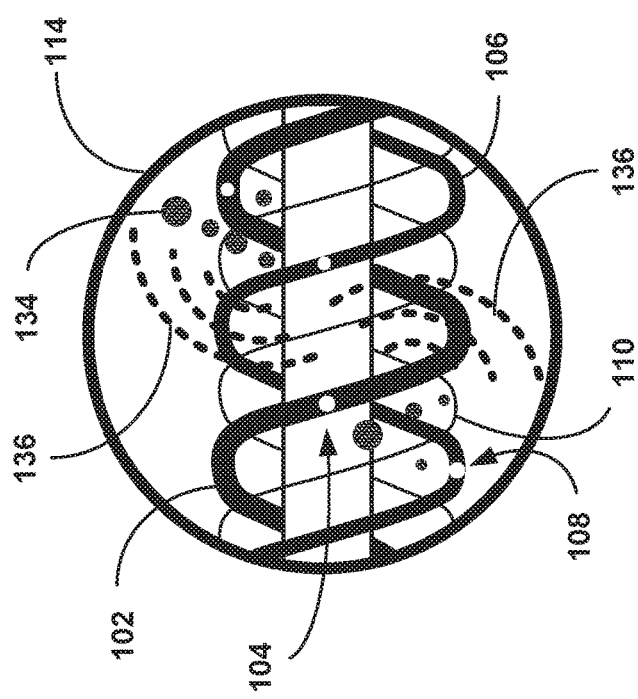
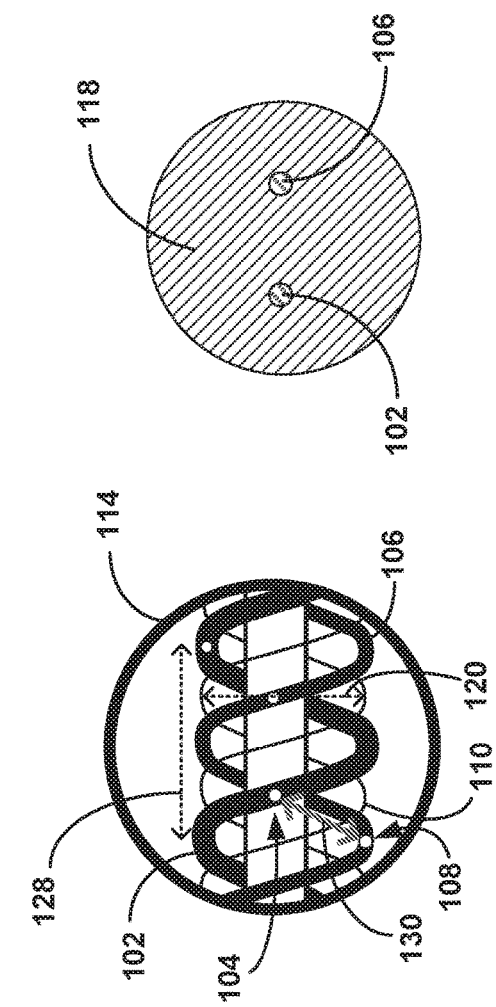
FIG. 2A
FIG. 2B
FIG. 2C
FIG. 2D

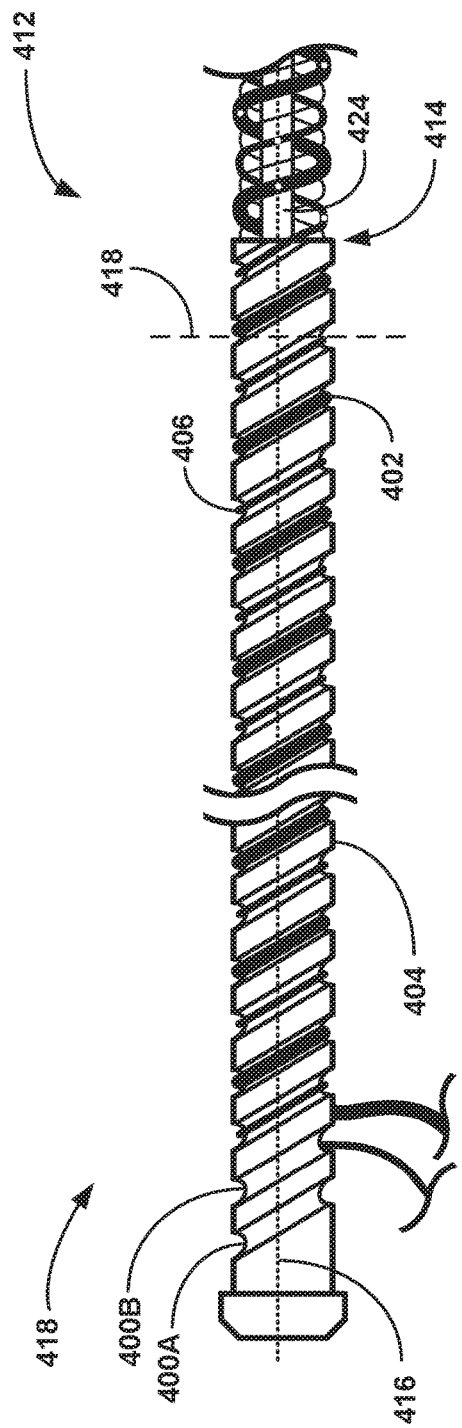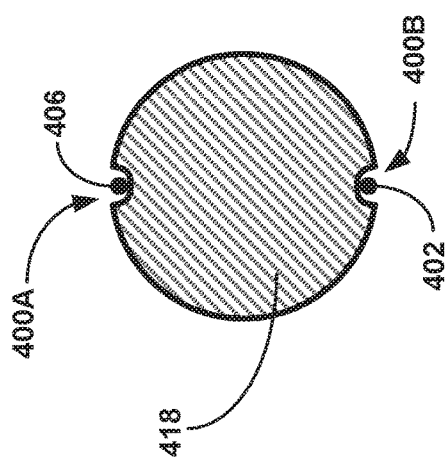
FIG. 7A
FIG. 7B

CAVITATION GUIDEWIRE

This application claims the benefit of U.S. Provisional Application No. 62/750,516, which was filed on Oct. 25, 2018, and is entitled, "CAVITATION GUIDEWIRE." The entire content of U.S. Provisional Application No. 62/750,516 is incorporated herein by reference.

TECHNICAL FIELD

This disclosure relates to medical guidewires.

BACKGROUND

Medical guidewires have been proposed for use with various medical procedures. For example, medical guidewires may be used to access target sites of a patient, such as sites within blood vessels or hollow anatomical structures of the patient. Other medical instruments may be navigated to these target sites once the guidewire has been successfully navigated to or near the target site. For example, after a guidewire is navigated to a target site of a body, another medical instrument such as a catheter may be slid over the guidewire until the distal end of the medical instrument is at the target site.

SUMMARY

In some aspects, the disclosure describes example medical devices, such as guidewires, that include two electrodes configured to deliver energy to fluid to induce cavitation within the fluid. In some examples, a guidewire includes an elongated member and a shaft that extends distally from the elongated member, where the elongated member and shaft are configured to together be navigated through cardiovasculature. The elongated member and shaft may be navigated to a defect such as a lesion in the cardiovasculature. The guidewire may include a first conductor that extends (e.g., coils) around the shaft to define an outer perimeter of the guidewire. The first conductor may be configured to be electrically connected to an energy source. The guidewire may also include a first electrode that is located adjacent to the shaft at a location where the first conductor extends around the shaft. The first electrode may be configured to be electrically coupled to the energy source via the first conductor. The guidewire may further include a second electrode and a second conductor that is configured to couple the second electrode to the energy source. Processing circuitry may be configured to control the energy source to cause the first and second electrode to deliver an electrical signal to a fluid that is contacting the first and second electrode to cause the fluid to undergo cavitation. Undergoing cavitation may include generating a pressure pulse wave within the fluid. In some other aspects, the disclosure describes methods of using the guidewires described herein.

Clause 1: In one example, a guidewire includes: an elongated member; a shaft extending distally from the elongated member, wherein the elongated member and the shaft are configured to be navigated through vasculature of a patient; a first conductor extending around the shaft to define an outer perimeter of the guidewire and configured to be electrically connected to an energy source; a first electrode located adjacent the shaft where the first conductor extends around the shaft, wherein the first electrode is configured to be electrically coupled to the energy source via the first conductor; a second electrode; and a second conductor configured to electrically couple the second electrode to the energy source, wherein the first and second electrodes are configured to deliver an electrical signal to a fluid in contact with the first and second electrodes to cause the fluid to undergo cavitation to generate a pressure pulse wave within the fluid.

Clause 2: In some example of the guidewire of clause 1, the first conductor includes an electrically conductive material at least partially covered with an electrically insulative material, and wherein the electrically insulative material defines an aperture that exposes the electrically conductive material to define the first electrode.

Clause 3: In some example of the guidewire of clause 2, the first electrode is one of a first plurality of electrodes that are each defined by one of a first plurality of apertures through the electrically insulative layer that exposes the electrically conductive layer of the first conductor, wherein the aperture is one of the plurality of apertures.

Clause 4: In some example of the guidewire of clause 3, the electrodes of the first plurality of electrodes are defined by apertures of the first plurality of apertures at a plurality of longitudinal locations and a plurality of radial locations along the shaft.

Clause 5: In some example of the guidewire of clause 1, the first electrode is a discrete component electrically coupled to the first conductor adjacent the shaft where the first conductor coils around the shaft.

Clause 6: In some examples of the guidewire of any of clauses 1-5, the proximal portions of the first conductor and the second conductor are embedded within the elongated member.

Clause 7: In some examples of the guidewire of any of clauses 1-5, wherein an outer surface of the elongated member defines a recess configured to receive at least part of the first conductor and the second conductor.

Clause 8: In some examples of the guidewire of clause 7, the recess defines a helix as the recess extends along a length of the elongated member.

Clause 9: In some examples of the guidewire of clause 8, a pitch of the helix decreases towards a distal end of the elongated member.

Clause 10: In some examples of the guidewire of any of clauses 1-9, the first and second conductors each extend around the shaft to define a respective coil, the coils defined by the first and second conductors having substantially equal pitches and inner diameters.

Clause 11: In some examples of the guidewire of any of clauses 1-10, the first and second conductors each comprise an electrically conductive material at least partially covered with an electrically insulative material, the electrically insulative material of the first conductor defining a first aperture that exposes the electrically conductive material of the first conductor to define the first electrode, and the electrically insulative material of the second conductor defining a second aperture that exposes the electrically conductive material of the second conductor to define the second electrode.

Clause 12: In some examples of the guidewire of clause 11, the first electrode is one of a first plurality of electrodes that are each defined by one of a first plurality of apertures through the electrically insulative layer of the first conductor that exposes the electrically conductive layer of the first conductor, and the second electrode is one of a second plurality of electrodes that are each defined by one of a second plurality of apertures through the electrically insulative layer that exposes the electrically conductive layer of the second conductor.

Clause 13: In some examples of the guidewire of clause 12, the electrodes of the first plurality of electrodes are defined by apertures of the first plurality of apertures at a plurality of longitudinal locations and a plurality of circumferential locations along the shaft, and electrodes of the second plurality of electrodes are defined by apertures of the second plurality of apertures at a plurality of longitudinal locations and a plurality of radial locations along the shaft.

Clause 14: In some examples of the guidewire of any of clauses 1-9, the second conductor comprises an electrically conductive core of the elongated member and the first conductor is embedded within the elongated member.

Clause 15: In some examples of the guidewire of clause 14, the elongated member includes at least one electrically insulative layer that electrically insulates the first conductor from the electrically conductive core of the second conductor.

Clause 16: In some examples of the guidewire of any of clauses 14 or 15, the shaft includes the second electrode.

Clause 17: In some examples of the guidewire of any of clauses 1-16, the first conductor extends around the shaft to define a first coil, the guidewire further comprising one or more spacing filars that each extend between turns of the first coil around the shaft to define a respective spacing coil, the first coil and the one or more spacing coils having substantially equal pitches and inner diameters.

Clause 18: In some examples of the guidewire of clause 17, the one or more spacing filars include at least three spacing filars.

Clause 19: In some examples of the guidewire of any of clauses 1-18, the guidewire further including a radiopaque distal tip that is distal to the shaft.

Clause 20: In some examples of the guidewire of any of clauses 1-19, the elongated member does not define a lumen that extends to a distal tip of the guidewire.

Clause 21: In some examples of the guidewire of any of clauses 1-20, the elongated member defines an outer diameter of about 0.25 millimeters and 0.75 millimeters.

Clause 22: In some examples of the guidewire of any of clauses 1-21, the guidewire defines a longitudinal length of a distal portion of about 5 millimeters to about 100 millimeters.

Clause 23: In some examples of the guidewire of any of clauses 1-22, the elongated member decreases in stiffness in a distal direction.

Clause 24: In some examples of the guidewire of any of clauses 1-23, the elongated member includes a hypotube.

Clause 25: In some examples of the guidewire of any of clauses 1-24, the shaft is a solid shaft.

Clause 26: In one example, a method includes: introducing a guidewire through vasculature of a patient to a target treatment site, the guidewire comprising: an elongated member; a shaft extending distally from the elongated member wherein the elongated member and the shaft are configured to be navigated through vasculature of the patient; a first conductor extending around the shaft to define an outer perimeter of the guidewire and configured to be electrically connected to an energy source; a first electrode located adjacent the shaft where the first conductor extends around the shaft, wherein the first electrode is configured to be electrically coupled to the energy source via the first conductor; a second electrode; and a second conductor configured to electrically couple the second electrode to the energy source; and controlling an energy source to deliver an electrical signal to a fluid in contact with the first and second electrode to cause the fluid to undergo cavitation and generate a pressure pulse wave within the fluid.

Clause 27: In some examples of the method of clause 26, the electrical signal is a first electrical signal and the method further includes: after delivering the first electrical signal, repositioning the guidewire within the vasculature; and after repositioning the guidewire within the vasculature, delivering a second electrical signal to cause the fluid to undergo further cavitation and generate further pressure pulse waves within the fluid.

Clause 28: In some examples of the method of any of clauses 26 or 27, the method further includes: navigating a distal portion of a catheter over the guidewire using a guidewire lumen of the catheter in response delivering the electrical signal to the fluid in contact with the first and second electrode; and deploying a medical device at the target treatment site from the distal portion of the catheter.

Clause 29: In some examples of the method of clause 28, the medical device comprises a balloon.

Clause 30: In some examples of the method of clause 28, the medical device comprises a stent.

Clause 31: In some examples of the method of any of clauses 26-30, delivering the electrical signal comprises delivering a plurality of electrical pulses having a pulse width of about 1 microsecond ($\mu s$) to about 200 $\mu s$.

The details of one or more examples are set forth in the accompanying drawings and the description below. Other features, objects, and advantages of examples according to this disclosure will be apparent from the description and drawings, and from the claims.

BRIEF DESCRIPTION OF THE DRAWINGS

FIG. 1A is a schematic side view of an example medical system that includes an example guidewire, an example energy source, and an example catheter.

FIG. 2A is a schematic side view of an example guidewire that includes two conductors and a spacing filar extending around a shaft at a distal portion of the guidewire as well as a plurality of electrodes defined by or coupled to the two conductors adjacent the shaft.

FIG. 2B is a schematic detail view of the example guidewire shown in FIG. 2A and illustrates the two conductors and the spacing filar extending around the shaft.

FIG. 2C is a schematic cross-sectional view of the two conductors embedded in the elongate member of the guidewire from FIG. 2A, where the cross-section is taken perpendicular to a longitudinal axis of the guidewire.

FIG. 2D is a schematic detail view of the example guidewire shown in FIG. 2A.

FIG. 7A is a schematic side view of two conductors of an example guidewire extending around a perimeter of the guidewire within respective recesses defined by the guidewire.

FIG. 7B is a schematic cross-sectional view of the two conductors within their respective recesses of the guidewire of FIG. 7A, where the cross-section is taken perpendicular to a longitudinal axis of the guidewire.

DETAILED DESCRIPTION

Figure 1B:
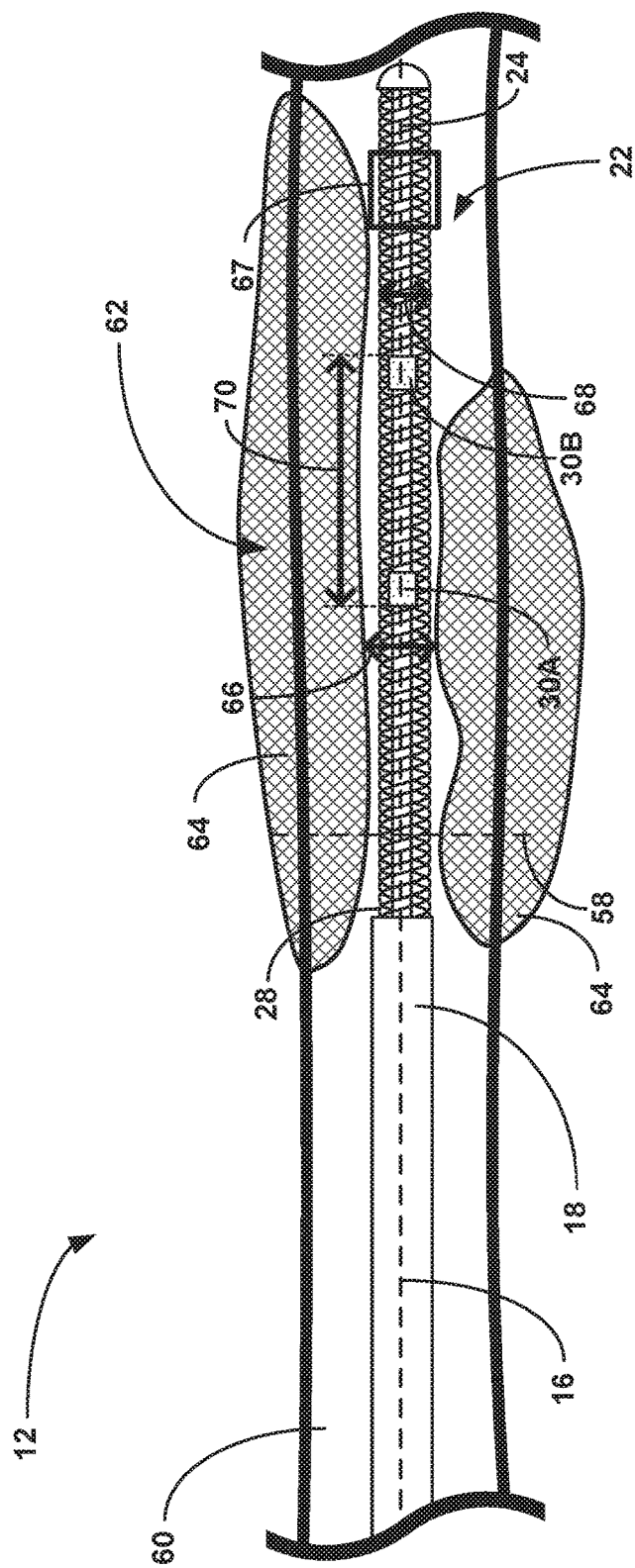
FIG. 1B is a schematic side view of the distal portion of the guidewire of FIG. 1A proximate to a lesion at a target site.

This disclosure describes guidewires, such as intravascular guidewires, which include a relatively flexible elongated member (e.g., the body of the guidewire) configured to be navigated through vasculature of a patient to a target treatment site within the cardiovasculature (e.g., within a blood vessel or within a heart) of a patient. The guidewire includes a shaft at a distal portion of the guidewire that extends distally from the elongated member. The guidewire may include at least two electrodes at the distal portion of the guidewire. The electrodes are configured to be electrically coupled to an energy source via respective conductors that extend along the guidewire.

At least one (and in some examples, all) of the conductors may extend around the shaft as the conductor(s) extend proximally from the electrodes. For example, at least one conductor may define a coil that extends around the shaft. The at least one conductor may define an outer perimeter of the guidewire as the at least one conductor extends (e.g., coils) around the shaft. The distal portion of the guidewire may be constructed such that at least one of the electrodes also defines a part of an outer perimeter of the guidewire at the distal portion. The electrodes may be configured to deliver an electrical signal to fluid (e.g., blood, saline, or a combination thereof) in contact with the electrodes. The energy transmitted to the fluid may rapidly heat the fluid to produce a short-lived gaseous steam/plasma bubble within the fluid that quickly collapses (e.g., cavitates), releasing energy in the form of a pressure pulse wave. The pulse wave may be used to treat a defect in the cardiovasculature of the patient at the target treatment site.

In some examples, the distal portion may include more than two electrodes and each conductor is electrically coupled to a plurality of electrodes. For example, the electrodes may be located at a plurality of longitudinal and circumferential locations. Each electrode may be configured to deliver an electrical signal with a paired electrode (e.g., the nearest electrode that is coupled to the opposite terminal of the energy source) to transmit energy to the fluid as described herein. In some examples in which the guidewire includes a plurality of pairs of electrodes, many or all of the pairs may be configured to transmit energy to fluid contacting the electrodes substantially simultaneously (e.g., simultaneous if not for the marginally different times at which the signal is provided from an energy source to different pairs of electrodes along the length of the guidewire).

By locating a plurality of pairs of electrodes at a plurality of longitudinal and circumferential locations and configuring many or all of the plurality of pairs of electrodes to transmit energy substantially simultaneously, the guidewire may treat a defect that defines a relatively long length (e.g., the defect is long enough such that it might be difficult for a single pair of electrodes to treat the defect without the guidewire being longitudinally repositioned) and extends fully or mostly around a circumference of a vessel of the vasculature (e.g., the defect extends around a full circumference of a vessel wall, such that it might be difficult for one or more pairs of electrodes that are at static circumferential locations relative to the guidewire to treat the defect without the guidewire being rotated) or around an annulus of a native heart valve of a patient. In some examples, the guidewire may be configured to only transmit energy to a selectable subset of the plurality of electrodes along the guidewire. For example, the guidewire may be configured to enable a clinician to select one or more of a proximal subset, medial subset, or distal subset of electrodes that correlate to a length of a lesion. Configuring the guidewire such that a number and/or array of electrodes may be selected based on such criteria as a length of the lesion may enable the guidewire to more efficiently treat a lesion as described herein.

In some examples, the target treatment site (hereinafter referred to as a target site) may be a site within the vasculature that has a defect that may be affecting blood flow through the vasculature or may be a site within a heart that may be affecting blood flow through the heart. For example, the target site may be a portion of the vasculature wall that includes a lesion, e.g., calcified plaque buildup. A lesion can cause partial or full blockages of blood bearing vasculature vessels, which can result in adverse physiological effects to the patient. As another example, the target site may be a portion of a heart valve, such as an aortic valve or mitral valve, that includes a calcified lesion, e.g., calcified plaque buildup on or within the valve. The calcium buildup may occur with age as the heart valves accumulate deposits of calcium which is a mineral found the blood. As blood repeatedly flows over the affected valve, deposits of calcium can build up on or within the leaflets or cusps of the valve, resulting in a stiffening (e.g., reduced pliability) of the leaflets. This stiffening narrows the valve, creating a stenosis that can result in adverse physiological effects to the patient. In addition, the calcification may reduce the elasticity of the native heart valve, which may interfere with the ability of a prosthetic heart valve that is implanted proximate to or within an annulus of the native heart valve to expand a desirable amount and define a desired flow diameter.

Some lesions within the vasculature or heart may be relatively difficult to treat using traditional methods, such as plain old balloon angioplasty, stenting, thrombectomy, atherectomy, or other interventional procedures. The pressure pulse wave resulting from the cavitation procedure using a guidewire described herein may impact the lesion (or other defect at the target site) to fracture or disrupt at least part of the lesion, which may lead to better outcomes for some patients.

Further, in some examples lesions may be difficult or impossible to access (e.g., become adjacent to) using medical devices that require the use of the Seldinger technique or the like prior to cavitation treatment as described herein. In this way, a medical device that defines a lumen (e.g., such as a catheter defining a guidewire lumen for navigational purposes) may inherently define too large of a cross-section to access the lesion. For example, it may be difficult for a medical device that defines a lumen to access or cross a lesion as a result of the lesion defining too little "clearance" (e.g., cross-sectional unobstructed area) within the vasculature. The lesion may define relatively little clearance as a result of the body vessel itself being relatively small and/or as a result of the lesion within the body vessel having a relatively large build-up. For example, a lesion may have clearance of about 0.38 millimeters (mm) (15 thousandths of an inch) to about 1 mm (40 thousandths of an inch) between internal walls of a lesion and/or vessel wall. Due to the relatively large cross-sectional size of medical devices that define a lumen (such as a guidewire lumen that may define a cross-sectional diameter of about 0.38 mm to about 1 mm), it may be relatively difficult to navigate such medical devices to access or cross such lesions.

Conversely, the guidewire described herein may be sized to fit within this clearance. For example, the diameter of a distal portion of a guidewire may be about 0.35 mm (about 14 thousandths of an inch) to about 0.75 mm (about 30 thousandths of an inch). As another example, the diameter of a distal portion of a guidewire may be 0.20 mm to about 1 mm, such as about 0.25 mm to about 0.35 mm, or about 0.25 mm to about 0.75 mm. In some examples, such as when used to describe numerical values, "about" or "approximately" refers to a range within the numerical value resulting from manufacturing tolerances and/or within 1%, 5%, or 10% of the numerical value.

In some examples, some or all of the guidewire may be substantially solid (e.g., may substantially avoid defining lumens or cavities) in order to define this small diameter. As a result of this reduced profile, the distal portion may be configured to navigated through (e.g., across) and/or adjacent lesions that define a relatively small clearance, and therein treat these lesions.

In some examples, the guidewire may further be used to navigate other medical devices to the target site. For example, a medical device (e.g., such as a catheter) that defines a larger outer cross-sectional size than the guidewire may be advanced over the guidewire once the guidewire has treated the lesion with the cavitation techniques described herein. Such a medical device (hereinafter referred to as a catheter for purposes of brevity) may include one or more deployable therapy devices, such as a balloon, a stent, a filter, a heart valve prosthesis, or the like. Additionally, or alternatively, a catheter may be able to execute some functionality, such as aspiration or providing/delivering a therapeutic agent or the like.

Once the guidewire has treated the lesion with the cavitation techniques described herein, the lesion may be more pliable, such that it is relatively easier to push the lesion radially outward (e.g., using a deployable therapy device such as a balloon, heart valve prosthesis, filter, or stent). For example, after the guidewire has treated the lesion with the cavitation techniques, the lesion may remain secured to the wall in a fractured or broken state, such that the lesion defines numerous pieces. These numerous pieces may be able to move relative to each other, such that the lesion may "flex" within the vasculature. As a result of the lesion flexing (or otherwise being relatively more flexible), a catheter or the like may be navigated over the guidewire to the target site.

The catheter or other device navigated over the guidewire may be used to sense one or more patient parameters (e.g., blood flow characteristics), to provide additional therapy, or to provide a guide for another treatment device, such as another catheter. For example, once the catheter is navigated to the target site, a stent, filter, balloon, heart valve prosthesis, or the like may be deployed from the catheter to expand and dilate the blood vessel, heart valve annulus, or other structure of the patient by "flexing" the now cracked lesion to a greater internal diameter. Dilating the blood vessel may improve blood flow in the blood vessel by providing the blood vessel with an increased flow diameter (relative to the diameter prior to the cavitation). A blood vessel may not be perfectly circular in cross-section, and the reference to a "diameter" of a blood vessel or a flow diameter may refer to the maximum cross-sectional dimension, which can be a diameter in some examples. In some examples, the clearance defined by the lesion would have been insufficient to enable the catheter to travel to the target site prior to cavitation. Using a guidewire to use cavitation to break or weaken a lesion that could not initially be accessed by the catheter such that the catheter subsequently can access and treat the lesion with a device such as a balloon, filter, stent, or a heart valve prosthesis or the like may improve the ability of a clinician to treat lesions that are impacting the health of a patient.

In some examples, post-cavitation, a stent can be delivered to the target site as part of a prosthetic heart valve. Post-cavitation, calcified leaflets of a native heart valve may become more elastic, allowing for easier manipulation when deploying the prosthetic heart valve. In addition, the more elastic native leaflets may better enable the stent of the prosthetic heart valve to expand more fully in place proximate to or within an annulus of the native heart valve, which may help prevent valvular leakage in the future.

FIG. 1A is a schematic side view of an example system 10 that includes guidewire 12 configured to be electrically coupled to cavitation energy source 14. Guidewire 12 defines longitudinal axis 16 and includes elongated member 18 that extends along longitudinal axis 16. Elongated member 18 may generally comprise the body of guidewire 12. In some examples, elongated member 18 includes a hypotube. In some examples, elongated member 18 is substantially solid (e.g., solid or solid to the extent permitted by variances in the material) throughout most or all of its longitudinal length, such that elongated member 18 substantially does not define any lumens or cavities or the like. For example, elongated member 18 may be solid such that it includes a single continuous material between an outer perimeter of elongated member 18 without substantially any cavities or lumens that extend along most or all of its longitudinal length. In certain examples, elongated member 18 may define a partial lumen that extends down a portion of the longitudinal length but does not extend from a proximal end of the elongated member 18 to a distal end of the elongated member 18, and/or where such a partial lumen is closed (e.g., does not define a distal port) at a distal end of the elongated member 18. For another example, elongated member 18 may include one or more longitudinal components (e.g., such as conductive wires or conductors as described herein) that are embedded within elongated member 18 along a length of elongated member 18 such that there are is little or substantially no space between embedded longitudinal components and the material of elongated member 18.

In some examples, elongated member 18 may be substantially cylindrical. For example, elongated member 18 may define a substantially circular cross-section, the cross-section being taken in a direction perpendicular to longitudinal axis 16. In other examples, elongated member 18 may define other cross-sectional shapes, such as a square or rectangular cross-sectional shape. Elongated member 18 may be made of one or more suitable materials. For example, elongated member 18 may be made of one or more biocompatible materials, such as, but not limited to, one or more metallic materials such as stainless steel, gold, platinum, and/or Nitinol, and/or elongated member 18 may be made of one or otherwise include one or more polymeric materials or coatings as described herein (e.g., a hydrophilic coating, a hydrophobic coating, a silicone coating, a tetrafluoroethylene coating, or the like).

Elongated member 18 extends from proximal end 20 of guidewire 12 to distal portion 22 of guidewire 12 (e.g., such that elongated member 18 distally ends at a proximal end of distal portion 22). Distal portion 22 includes shaft 24 distally extending from distal end 27 of elongated member 18 along longitudinal axis 16 of guidewire 12. In some examples, shaft 24 is coaxial with elongated member 18. In other examples, however, a central longitudinal axis of shaft 24 may be offset from a central longitudinal axis of elongated member 18, such that elongated member 18 and shaft 24 are not coaxial. Shaft 24 may be substantially solid (e.g., solid but for variances in the material from which shaft 24 is formed), which is to say shaft 24 may not purposefully defined lumens or cavities. In some examples, elongated member 18, shaft 24, and distal tip 26 of guidewire 12 may be a substantially unitary structure.

In some examples, shaft 24 defines a smaller outer cross-sectional dimension than elongated member 18. For example, if both elongated member 18 and shaft 24 define generally circular cross-sectional shapes, and elongated member 18 may define a larger diameter than shaft 24. Shaft 24 may extend up to distal tip 26 of guidewire 12. In some examples, at least a portion of distal tip 26 is radiopaque so that a clinician may track a location of distal tip 26 (and therein track a location of distal portion 22 and components thereon) using fluoroscopy techniques. In some examples, distal tip 26 may include a relatively soft material along a distal surface to define an atraumatic tip of guidewire 12.

A plurality of coil elements 28 may extend around shaft 24, e.g., to define a coil shape. In some examples, coil elements 28 define an outer perimeter of guidewire 12 at distal portion 22. As discussed in greater detail below, coil elements 28 may include electrical conductors that are configured to be electrically coupled to energy source 14. Alternatively, and/or additionally, coil elements 28 may include spacing filars configured to maintain a predetermined structure and distance between components (e.g., such as electrodes) of distal portion 22. For example, coil elements 28 may include one or two conductive filars and two or more spacing filars as both the electrically conductive filars and the spacing filars extend from elongated member 18 (e.g., such that the electrically conductive filars were embedded within or were received in a surface recess of elongated member 18 as described below) with conductive filar being separated by two or more spacing filars (e.g., such that there would be at least one spacing element on either side of each conductive filar) as each of the electrically conductive filars and spacing filars coil along distal portion 22. For another example, elongated member 18 may include an electrically conductive and electrically insulated hypotube that transitions into electrically conductive and electrically insulated coil elements 28 at distal portion 22. As depicted herein, coil elements 28 may coil the full longitudinal distance between elongated member 18 and distal tip 26. In some examples, coil elements 28 may only coil a partial longitudinal distance along distal portion 22 (e.g., coil elements 28 may only coil up to one or more electrodes).

Distal portion 22 includes at least two electrode 30A, 30B (collectively, "electrodes 30"). At least one of the two electrodes 30 may be located at an outer perimeter of guidewire 12 at distal portion 22. At least one of the electrodes 30 at an outer perimeter of guidewire 12 may be electrically coupled to one or more coil elements 28. In some examples, one or more electrodes 30 may be located on shaft 24. Electrodes 30 located on shaft 24 may be electrically coupled to shaft 24. Each of electrodes 30 may include at least one surface that is configured to be exposed to a fluid when distal portion 22 is navigated to a target site in a patient. In some examples, portions of one or all electrodes 30 may be radiopaque, whether in addition to or instead of distal tip 26 being radiopaque.

In some examples, guidewire 12 may include hub 32 positioned at a proximal end of guidewire 12 adjacent proximal portion 34 of guidewire 12. Hub 32 may be mechanically connected to a proximal end of guidewire 12 via an adhesive, via overmolding (of hub 32), via welding, or via another suitable technique or combination of techniques. One or more of cables 36A, 36B (collectively, "cables 36") may be used to electrically connect electrodes 30 to energy source 14 (which is discussed in greater detail in FIG. 12). In some examples, cables 36 may be removably coupled to hub 32 and/or energy source 14. In other examples, cables 36 may be fixedly secured to one of hub 32 or energy source 14.

As coupled to energy source 14, guidewire 12 may include at least one electrode 30 operating as a supply or positive electrode and another electrode operating as a return or negative electrode. In such examples, the electrical signal delivered by energy source 14 may be delivered between electrodes 30 as an arc, spark, corona, plasma, or the like using fluid of the vasculature as the electrically conductive medium. The fluidic separation distance between electrodes 30 (e.g., the distance that fluid needs to travel to get between electrodes 30) may determine what manner of electrical signal should be delivered, whether arc, spark, corona, plasma, or the like. In examples in which an exposed surfaces of electrodes 30 may be separated by less than about 0.5 mm (as measured along longitudinal axis 16), arc discharge may be desired. Alternatively, in examples in which exposed surfaces of electrodes 30 may be separated by the same distance (e.g., less than about 0.5 mm) or a much greater distance (e.g., separated by a distance of about 1 mm to about 5 mm), a corona discharge may be desired. The total number of electrodes 30 may be chosen depending on the size of the lesion being treated at the target site and the type of electrical signal delivery desired.

In this way, guidewire 12 may utilize a bipolar electrode design where electrical signals travel between pairs of electrodes 30 secured to guidewire 12. Alternatively, or additionally, in some examples system 10 may include one or more external electrodes (e.g., such as a return pad outside of the vasculature of the patient, or a lollipop electrode inserted into a subcutaneous pocket of the patient, or the like) and utilize a monopolar or multipolar electrode construction. Though bipolar techniques are substantially discussed herein for purposes of brevity, it is to be understood that many of the systems and methods described herein may additionally utilize monopolar or multipolar electrodes using one or more external electrodes.

As described herein, each of electrodes 30 may include at least one surface that is configured to be exposed to fluid when guidewire 12 is introduced in cardiovasculature of a patient. The site for cavitation (e.g., the location adjacent distal portion 22 at which energy pulses are created) may be controlled by controlling the surface area and/or materials of exposed surfaces of electrodes 30. For example, where two electrodes 30 have different surface areas from each other, whichever of electrodes 30 has the smaller surface area may have a higher current density for a given electrical signal and therefore act as the site for cavitation to occur. Additionally, or alternatively, the direction of the resultant pressure pulse waves produced by the cavitation may be controlled based on the circumferential location of the exposed surfaces of electrodes 30 along elongated member 18. For example, as discussed herein, electrodes 30 may define exposed surfaces oriented in different circumferential directions along guidewire 12 to allow for 360° deployment of the pressure pulse waves within the vasculature of the patient. Additionally, or alternatively, the positioning of electrodes 30 at different circumferential orientations along guidewire 12 may enable the electrical signal transmitted between electrodes 30 to "cascade" circumferentially around guidewire 12.

In some examples, the intensity of the pressure pulse waves may be adjusted by controlling the intensity of the electrical signal delivered via electrodes 30, the separation distance between electrodes 30, the exposed surface area of the respective electrode 30, and the like or combinations thereof. The intensity of the electrical signal may be function of one or more of a voltage, a current, a frequency (e.g., a pulse rate in the case of pulses), a pulse width (e.g., a pulse width of about 1 microsecond (μs) to about 200 μs), or one or more other electrical signal parameters. For example, energy source 14 may be configured to generate and deliver pulses having an amplitude of about 500 volts (V) to about 5000 V (e.g., about 1500V to about 3000 V), a pulse width of about 1 microsecond (μs) to about 5 μs for arc-type cavitation or about 10 μs to about 200 μs for corona-type cavitation, and a frequency of about 0.5 Hertz (Hz) to about 1000 Hz. In certain examples, one of the electrodes associated with the cavitation procedure (e.g., the reference electrode) may be external to the patient. For example, guidewire 12 may include electrode 30 positioned within vasculature of the patient and a reference or return electrode may be positioned on the external skin surface of the patient, e.g., as a pad electrode. The electrical signal may be delivered between electrodes 30 and the external reference or return electrode, through fluid of the patient and the tissue of the patient to induce cavitation of fluid at one of electrodes 30.

Proximal portion 34 and distal portion 22 of guidewire 12 as discussed and depicted herein may be of any suitable length. For example, distal portion 22 may be about 5 mm to about 100 mm, such as about 10 mm to about 50 mm or about 10 mm to about 30 mm, depending upon, e.g., a longitudinal length of the lesions expected to be treated using guidewire 12. Further, proximal portion 34 may be long enough to navigate distal portion 22 to the target site and/or enable another medical device to be navigated over proximal portion 34 subsequent to cavitation. For example, proximal portion may be about 50 centimeters (cm) to about 400 cm. In some examples, guidewire 12 may also include one or more intermediate (e.g., medial) portions separating proximal portion 34 and distal portion 22.

In some examples, guidewire 12 may be used to access relatively distal vasculature locations in a patient or other relatively distal tissue sites (e.g., relative to the vasculature access point). Example vasculature locations may include locations in a coronary artery, peripheral vasculature (e.g., carotid, iliac, or femoral artery, or a vein), cerebral vasculature, or a heart valve (e.g., aortic valve, mitral valve, tricuspid valve, or the like). In some examples, some or all of guidewire 12 may be structurally configured to be relatively flexible, pushable, and relatively kink-resistant and buckle-resistant. Structurally configuring guidewire 12 in this way may reduce or eliminate a likelihood of guidewire 12 buckling when a pushing force is applied to hub 32 and/or proximal portion 34 of guidewire 12 to advance distal portion 22 distally through vasculature. Further, structuring some or all of guidewire 12 in this way may reduce or eliminate a likelihood of guidewire 12 kinking when be navigated around a tight turn in the vasculature. Reducing a likelihood of guidewire 12 kinking and/or buckling while being navigated through vasculature may improve an ability of a clinician to navigate distal portion 22 of guidewire 12 to a target site in a patient.

The greatest-cross-sectional dimension (this greatest cross-sectional diameter hereinafter referred to as an outer diameter, though guidewire 12 may define non-circular cross-sectional shapes) of guidewire 12 may be of any suitable size or dimension including, for example, about 0.2 mm to about 1 mm, such as about 0.35 mm to about 0.75 mm, or about 0.25 mm. In some examples, the outer diameter may be substantially constant (e.g., uniform outer diameter), tapered (e.g. tapered or step change to define a narrower distal portion), or combinations thereof. For example, guidewire 12 may taper from a relatively larger diameter (e.g., about 0.4 mm to about 0.9 mm) at a proximal end of guidewire 12 to a relatively smaller diameter (e.g., about 0.35 mm and about 0.75 mm at distal portion 22 of guidewire 12. As described herein, the relatively small diameter of guidewire 12 may improve navigability of guidewire 12 to a target site across or into cardiovasculature having a relatively small amount of clearance (e.g., unblocked cross-sectional vasculature at a given point) due to relatively large lesions, relatively small vasculature, and/or relatively tortuous vasculature.

In some examples, at least a portion of an outer surface of guidewire 12 may include one or more coatings, such as, but not limited to, an anti-thrombogenic coating, which may help reduce the formation of thrombi in vitro, an antimicrobial coating, and/or a lubricating coating. In some examples, the entire working length of guidewire 12 may be coated with the hydrophilic coating. The hydrophilic coating may be configured to reduce static friction and/or kinetic friction between guidewire 12 and tissue of the patient as guidewire 12 is advanced through the vasculature. In other examples, only a portion of the working length of guidewire 12 (e.g., some of elongated member 18, or some coil elements 28 of distal portion 22) may be coated with the hydrophilic coating. This may provide a length of guidewire 12 distal to hub 32 that does not include a hydrophilic coating and with which the clinician may grip guidewire 12 in order to push, rotate, or otherwise handle guidewire 12 through and within the vasculature.

As discussed above, guidewire 12 has a suitable length for accessing a target tissue site within the patient from a vasculature access point. The length may be measured along longitudinal axis 16 of guidewire 12. The working length of guidewire 12 may depend on the location of the lesion within vasculature. For example, if guidewire 12 is a guidewire used to access a coronary, carotid, or abdominal artery, guidewire 12 may have a working length of about 50 cm to about 400 cm, such as about 110 cm, although other lengths may be used. The working length may include a length sufficient to enable a catheter 38 or the like to be navigated to a target site over guidewire 12. For example, guidewire 12 may define a working length that results in proximal portion 34 extending out of a patient a length sufficient for a clinician to easily grasp and handle for purposes of inserting proximal portion 34 into a distal port at distal end 40 of catheter 38 and extending guidewire 12 through a full length of catheter 38 before distal end 40 of catheter 38 enters a patient.

In some examples, as depicted in FIG. 1A, distal portion 42 of catheter 38 may include balloon 44 or another treatment portion that may be deployed at target site once guidewire 12 has delivered cavitation energy as described herein to fracture a lesion at the target site. Additionally, and/or alternatively, catheter 38 may be configured to provide execute an operation at the lesion, such as providing aspiration or delivering a therapeutic agent. Using guidewire 12 to deliver cavitation and then immediately using guidewire 12 to introduce catheter 38 for deploying a therapy device such as balloon 44 or a stent or a heart valve prosthesis or the like or otherwise using catheter 38 to execute therapeutic functionality at the lesion may improve an ability of a clinician to treat a patient. For example, the deployment of a heart valve prosthesis immediately following the cavitation procedure may help improve treatment efficacy and potential patient outcomes.

FIG. 1B is an enlarged conceptual side view of distal portion 22 of guidewire 12 of FIG. 1 within blood vessel 60 of vasculature of a patient at an example target site 62. Target site 62 includes an example lesion 64, which may be a calcified mass of tissue on or within a wall of blood vessel 60. In some cases, lesion 64 may extend around a full perimeter of blood vessel 60 at target site 62, or may extend only partially around a perimeter of blood vessel 60. The size, shape, length, and location of lesion 64 relative to walls of blood vessel 60 within FIG. 1B is one example. In other examples, lesion 64 may define other sizes, shapes, lengths, or relative locations on or within the walls of blood vessel 60. In some examples, lesion 64 may be superficial. In other examples, lesion 64 may be a deep calcification within the tissue of blood vessel 60. In certain examples lesion 64 may be on or within a heart valve (e.g., aortic valve).

Figure 1D:
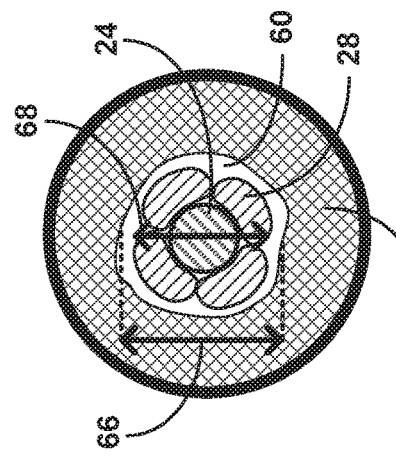
FIG. 1D is a schematic cross-sectional view of the guidewire of FIG. 1A and the lesion of FIG. 1B, where the cross-section is taken perpendicular to a longitudinal axis of the guidewire.
Figure 1C:
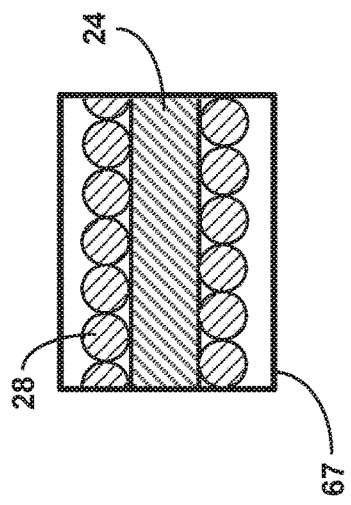
FIG. 1C is a schematic cross-sectional view of the coil elements and shaft of the distal portion of the guidewire of FIG. 1A, where the cross-section is taken along a longitudinal axis of the guidewire.

The amount of space between coil elements 28 and shaft 24 is depicted for purposes of illustration (e.g., to depict the coiling nature of coil elements 28 relative to each other and shaft 24). In some examples, there may be less space or no space between adjacent portions of coil elements 28 and shaft 24. For example, FIG. 1C depicts conceptual cross-sectional detail view 67 of FIG. 1B taken along longitudinal axis 16 of guidewire 12. As depicted in FIG. 1C, in some examples, adjacent coil elements 28 may contact each other. Similarly, as depicted in FIG. 1C, in some examples, coil elements 28 may contact an adjacent portion of shaft 24. In other examples, coil elements 28 may define some amount of longitudinal space between adjacent coil elements 28, and/or coil elements 28 may define some amount of radial space between coil elements 28 and shaft 24.

Turning back to FIG. 1B, as depicted, lesion 64 and blood vessel 60 may define clearance 66 (e.g., cross-sectional distance of unobstructed body vessel) that is only slightly bigger than cross-sectional width 68 of distal portion 22 of guidewire 12. For example, FIG. 1D is a conceptual cross-sectional view taken along cut-plane 58 of shaft 24 and coil elements 28. As discussed above, FIG. 1D depicts lesion 64 extending around a full perimeter of blood vessel 60. In some examples, as depicted, clearance 66 may be only slightly greater than cross-sectional width 68 across substantially any diameter of blood vessel 60 and guidewire 12, though in other examples clearance 66 may be greater across some dimensions than others. Additionally, or alternatively, in some examples clearance 66 may be smaller than cross-sectional width 68. In examples where clearance 66 is smaller than cross-sectional width 68, distal portion 22 may be configured to cross lesion 64 independently (e.g., by outwardly deforming lesion 64 slightly, as a result of distal portion 22 compressing as distal portion 22 crosses lesion 64, and/or as a result of lubricious coating on some or all external surfaces of distal portion 22) and/or with the aid of another device that expands clearance 66 or pulls distal portion 22 across lesion 64 or the like.

Turning back to FIG. 1B, as discussed above, distal portion 22 of guidewire 12 includes electrodes 30. Electrodes 30 of guidewire 12 may be configured to contact an electrically conductive fluid within blood vessel 60 (e.g., blood or saline introduce by a clinician). Electrodes 30 are configured to deliver energy (generated by energy source 14 in FIG. 1A) to this fluid to cause the fluid to undergo cavitation. In some examples, at least one of electrodes 30 may be located at an outer perimeter of distal portion 22. For example, electrode 30A may be located at an outer perimeter of distal portion 22 of guidewire 12, and at this location electrode 30A may be electrically connected to, supported by, and/or defined by one or more of coil elements 28. In certain examples, at least one of electrodes 30 may be located on shaft 24. Electrodes 30 located on shaft 24 may be electrically connected to, supported by, and/or defined by shaft 24.

The term electrode may refer to the component(s) or portions of the component(s) that are used to delivery energy to induce cavitation. Electrodes 30 as referred to herein, is not intended to imply that each of electrodes 30 is a discrete physical component (e.g., a stand-alone, distinct element), or to imply that all of cavitation system is within blood vessel 60. For example, as described below, coil elements 28 and/or shaft 24 may include conductors that have an electrically insulative layer around an electrically conductive layer, where electrodes 30 are defined by a portion of the electrically conductive layer exposed by an aperture in the electrically insulative layer. While electrodes 30 may refer to one or more portions of conductor(s) (as described above or below) and/or marker band(s) or the like positioned in blood vessel 60, energy source 14 may not be located within blood vessel 60 and may be exterior to the body of a patient.

During the cavitation procedure, energy in the form of, for example, energy source 14 may generate and deliver an electrical signal to the fluid of blood vessel 60 via electrodes 30 to heat a portion of the fluid to generate a steam/plasma bubbles within the fluid. As described above, electrodes 30 may transmit energy (e.g., electrical energy) to a fluid that rapidly heats a portion of this fluid to produce short-lived gaseous steam/plasma bubbles within the fluid to create an initial pressure pulse wave. The steam/plasma bubbles may represent relatively low-pressure pockets of vapor generated from the surrounding fluid. The low-pressure steam/plasma bubbles eventually collapse in on themselves due to the relatively high pressure of the surrounding fluid. As steam/plasma bubbles collapse, the bubbles release an energy in the form of a subsequent pressure pulse wave within the fluid. Pressure pulse waves propagate through the fluid where they impact the tissue at target site 62 transmitting the mechanical energy of pressure pulse waves into the tissue and lesion 64. The energy transmitted to lesion 64 may cause lesion 64 to fracture or beak apart.

The pressure pulse waves may propagate through fluid where they impact the wall of lesion 64 transmitting the mechanical energy of the pressure pulse wave into the tissue of blood vessel 60 (or a heart in other examples) and/or lesion 64 on or within the vessel wall. The energy transmitted to lesion 64 may cause the lesion to fracture or break apart. As a result of lesion 64 fracture or breaking apart, another medical device such as catheter 38 may be navigated to lesion 64 and may deploy a medical device such as balloon 44 at target site 62 to expand walls blood vessel 60 and further break-up lesion 64 to define a larger flow diameter through blood vessel 60.

By conducting the cavitation procedure in blood vessel 60 using fluid in direct and intimate contact with the wall of lesion 64 and/or blood vessel 60, the transfer of energy from the pressure pulse waves to lesion 64 may be more efficient as compared to a cavitation procedure that introduces one or more intermediate devices (such as a sidewall of a balloon that may otherwise dampen the pulse energy) between the source of cavitation (e.g., electrodes 30) and lesion 64. In some examples, the improved efficiency of the process may require less energy to be transmitted to fluid to incur the same amount of cavitation force. Further, as the temperature of fluid increases as a consequence of the cavitation procedure, the overall energy delivered to fluid may reduce. Reducing the overall energy delivered to the fluid of blood vessel 60 may reduce the temperature increase to fluid caused by the delivery of energy to the fluid. Further, the increased efficiency of the energy transfer between the pressure pulse waves to lesion 64 may reduce a duration of which the cavitation procedure must be performed in order to sufficiently fracture or break apart lesion 64 resulting in an overall shorter procedure.

Additionally, or alternatively, due to the improved efficiency of the cavitation process, the profile of guidewire 12 may be reduced. For example, the lower power requirements may mean that the components powering electrodes 30 (e.g., the conductors supplying electrodes 30) may require a lower energy load, thereby allowing for smaller gauge of components to be incorporated into guidewire 12. In some examples, the lowered power demands may also enable guidewire 12 and the associated energy source 14 to be operated as a handheld unit.

The specific size, shape, and location of electrodes 30 of FIGS. 1A and 1B is for purposes of illustration only. Electrodes 30 may have any suitable size, shape, or longitudinal and circumferential location relative to shaft 24. In some examples, all or some of electrodes 30 may define the same size and/or shape, while in other examples all or some of electrodes 30 may define different sizes and/or shapes. The longitudinal section of distal portion 22 that includes all electrodes 30 may have any suitable length 70 (measured along longitudinal axis 16), which may depend, for example, on the length of lesion 64 or the size and shape of blood vessel 60. For some procedures used to treat lesions 64 in or near a heart valve (e.g., aortic valve) of a patient, electrodes 30 of distal portion 22 may define longitudinal length 70 of about 5 mm to about 100 mm. For some procedures used to treat lesions 64 in or near the coronary vasculature, electrodes 30 of distal portion 22 may define longitudinal length 70 of about 1 mm to about 4 mm.

Electrodes 30 may be coupled to energy source 14 via any suitable one or more of a variety of constructions. Guidewire 12 may include two conductors that electrically couple electrodes 30 to energy source 14. In some examples, coil elements 28 are the conductors. For example, as shown in FIG. 2A, an example guidewire 112 may include a first conductor 102 that is configured to electrically couple a first plurality of electrodes 104A, 104B (collectively, "electrodes 104") to energy source 14 and second conductor 106 that is configured to electrically couple a second plurality of electrodes 108A, 108B (collectively, "electrodes 108") to energy source 14. Conductors 102, 106 coil around shaft 124, which distally extends from elongated member 118. Conductors 102, 106 may include low-profile wires such as ribbon wires. By utilizing low profile wires for conductors 102, 106, elongated member 118 may be able to use a relatively greater amount of its cross-sectional area to define walls (e.g., rather than that cross-sectional area being occupied by relatively higher-profile wires), therein improving an ability of guidewire 112 to transmit torque along its length. Guidewire 112 may be substantially similar to guidewire 12, elongated member 118 may be substantially similar to elongated member 18, shaft 124 may be substantially similar to 24, and conductors 102, 106 may be substantially similar to coil elements 28, with the exception of any differences described herein.

Conductors 102, 106 and electrodes 104, 108 may be formed using any suitable electrically conductive material including, for example, titanium alloys (e.g., Ti—Mo alloy), platinum or platinum-iridium alloys, stainless steel, copper, copper alloys (e.g., copper and hafnium or tungsten), tungsten, or the like. In certain examples, conductors 102, 106 may be formed of copper wire with a platinum coating or the like. Conductors 102, 106 and electrodes 104, 108 may be formed of the same material, while in other examples conductors 102, 106 and/or and electrodes 104, 108 may be formed of different materials. In some examples, conductors 102, 106 may be formed using metal wires extending along longitudinal axis 16 of guidewire 12.

Guidewire 112 may define longitudinal axis 116, along which elongated member 118 and shaft 124 may longitudinally extend. In some examples, elongated member 118, shaft 124, and distal tip 126 of guidewire 112 may be a substantially unitary structure. In other examples, shaft 124 may be physically separate from and securely attached to one or more of elongated member 118 or distal tip 126. For example, shaft 124 may be welded or bonded or the like to one or both of elongated member 118 and/or distal tip 126.

Conductor 102 may couple to one terminal of energy source 14, while the other conductor 106 couples to the opposing terminal of energy source 14. For example, conductor 102 may be coupled to a supply or positive terminus while conductor 106 may be coupled to a return or negative terminus, or vice versa. In this way, electrodes 104 may be coupled to supply conductor 102 and electrodes 108 may be coupled to return conductor 106 to enable the delivery of electrical energy through a fluid contacting electrodes 104, 108 to induce cavitation.

In the example shown in FIG. 2A, guidewire 112 includes spacing filars 110A, 110B (collectively, "spacing filars 110") that coil between conductors 102, 106. Spacing filars 110 and conductors 102, 106 may be relatively flexible to enable distal portion 122 of guidewire 112 to flex as guidewire 112 is navigated to target site 62. Spacing filars 110 may be made of any suitable material discussed herein, such as, but not limited to, a biocompatible material such as platinum, another metal, or a polymer. Though conductor 102, conductor 106, and spacing filars 110 are depicted with different thicknesses for purposes of illustration (e.g., so that each may be visually differentiated), conductor 102, conductor 106, and/or spacing filars 110 may be substantially the same size (e.g., thickness) in some examples.

Spacing filars 110 and conductors 102, 106 may all coil in a substantially similar manner along shaft 124. For example, FIG. 2B illustrates detail view 114 (from FIG. 2A) that depicts the coils of each of conductor 102, conductor 106, and spacing filars 110. As depicted, the coils of each of conductor 102, conductor 106, and spacing filars 110 may define substantially similar internal diameters 120 and substantially similar pitches 128 (e.g., where the pitch is the distance traveled by the respective coil when the respective coil completes a full revolution around shaft 124). A pitch of a coil may impact the flexibility of the coil, and, therefore, of guidewire 112 in examples in which the guidewire includes the coil.

Guidewire 112 may include at least one of spacing filars 110 adjacent each conductor 102, 106, such that conductors 102, 106 always have at least one of spacing filars 110 between them. In some examples (not depicted), guidewire 112 may include a plurality of spacing filars 110 between conductors 102, 106. Guidewire 112 may include a greater or fewer number of spacing filars 110 between conductors 102 to increase or decrease a distance between conductors 102, 106. Increasing or decreasing a distance between conductors 102, 106 may therein increase or decrease distance 130 between electrodes 104, 108 of conductors 102, 106. For example, distance 130 between paired electrodes 104, 108 (e.g., a nearest set of electrodes that are paired to opposite terminals of energy source 14) may be about 1 mm to about 2 mm. Configuring spacing filars 110 to space conductors 102, 106 apart such that paired electrodes 104, 108 are about 1 mm to about 2 mm apart may ensure that guidewire executes cavitation procedures as desired.

Turning back to FIG. 2A, distal portion 122 of guidewire 112 may include electrodes 104, 108 at a plurality of longitudinal locations and at a plurality of circumferential locations. Thus, guidewire 112 includes electrodes 104, 108 that are positioned to cause a fluid to undergo cavitation at many longitudinal locations along longitudinal axis 116 as well as at a plurality of different locations around an outer circumference of distal portion 122 of guidewire 112 (e.g., different radial locations as viewed along longitudinal axis 116 of guidewire 112). In some examples, guidewire 112 may be configured to cause a fluid to undergo cavitation along substantially the entire longitudinal length of distal portion 122 as well as extending 360° around the perimeter of distal portion 122 due to the number and location of electrodes 104, 108 on distal portion 122. Constructing guidewire 12 to include electrodes 104, 108 configured to cause fluid contacting electrodes 104, 108 to undergo cavitation along substantially an entire length and circumference of distal portion 122 may increase a speed at which lesion 64 may be treated.

The specific number and arrangement of electrodes 104, 108 on distal portion 122 is for purposes of illustration only. In some examples, the number of electrodes 104, 108 included on guidewire 12 may depend on the size and shape of lesion 64 intended to be treated using guidewire 12. For example, for longer lesions 64, a clinician may select a guidewire 112 including more electrodes 104, 108 to minimize the number of times the clinician needs to reposition guidewire 12 during the medical procedure that includes cavitation generated by energy delivered via electrodes 104, 108. In some examples, conductors 102, 106 and spacing filars 110 may extend to distal tip 126, such that electrodes 104, 108 are located adjacent distal tip 126. Configuring conductors 102, 106 and spacing filars 110 to extend to distal tip 126 such that electrodes 104, 108 are located adjacent distal tip 126 may enable a clinician monitoring a radiopaque element of distal tip 126 (e.g., using fluoroscopy techniques) to determine a location of the working length of electrodes 104, 108 (and therein where cavitation will occur). In other examples, conductors 102, 106, spacing filars 110, and/or electrodes 104, 108 may terminate distally (e.g., extend distally no further than) a location that is more proximal to distal tip 126.

Although FIGS. 2A, 2B, and 2D depict all electrodes 104, 108 as being substantially the same size, in some examples some electrodes 104, 108 may be sized differently than other electrodes 104, 108. For example, as described below, an amount of surface area that is defined by electrodes 104, 108 may impact the manner in which cavitation occurs when electrodes 104, 108 provide an electrical signal to tissue of the vasculature of the patient. As such, electrodes 104, 108 may define a plurality of different surface areas such that guidewire 112 may be configured to provide cavitation in a plurality of manners, depending upon which electrodes 104, 108 are selected by energy source 14 (e.g., automatically by energy source 14 or by a clinician using energy source 14) to provide cavitation.

Similar to FIG. 1C, in some examples, conductor 102, conductor 106, and spacing filars 110 may contact shaft 124 as conductors 102, 106, and spacing filars 110 longitudinally extend along distal portion 122. Similarly, in some examples, conductors 102, 106, and spacing filars 110 may contact longitudinally adjacent respective spacing filars 110 and conductors 102, 106 as each extends longitudinally along distal portion 122. To help fix the relative position of spacing filars 110 and conductors 102, 106 (and therein control a distance between electrodes 104, 108 and to promote proper cavitation), spacing filars 110 may be secured relative to shaft 124 in some examples. For example, spacing filars 110 may be structurally connected (e.g., welded or adhesively bonded or the like) to distal tip 126 and elongated member 118. In some examples, spacing filars 110 may also be structurally connected (welded or bonded or the like) to shaft 124 at one or more longitudinal locations along shaft 124, though spacing filars 110 may be predominantly unsecured from shaft 124 along a length of shaft 124 to maintain a desired stiffness of distal portion 122 (e.g., where welding spacing filars 110 to shaft 124 along a full length of shaft 124 increases stiffness past a desired threshold). For example, spacing filars 110 may be secured by, e.g., a first weld between each spacing filar 110 and elongated member 118, a second localized weld between each spacing filar 110 and shaft 124 in the middle of shaft 124 (where spacing filars 110 are not directly welded to shaft 124 outside of this second localized weld), and a third weld between each spacing filar and distal tip 126. Similarly, one or both of conductors 102, 106 may be secured to elongated member 118, shaft 124 (e.g., at one or more longitudinal locations), and/or distal tip 126. In some examples, one or both of conductors 102, 106 may be secured to one or more spacing filars 110.

Further, while FIGS. 1B-1D (and other figures described herein) are described regarding guidewire 12 navigated to blood vessel 60 of vasculature of a patient, in other examples guidewire 12 may be navigated to target site 62 in other areas of a patient. For example, guidewire 12 may be navigated to target site 62 in an organ of a patient. In some examples, guidewire 12 may be navigated to target site 62 in a heart of a patient, such as at a heart valve of the heart.

In some examples, conductors 102, 106 extend to a proximal end of guidewire 112, while in other examples, conductors 102, 106 terminate distal to the proximal end of guidewire 112 and are electrically connected to other electrical conductors in order to electrically couple electrodes 104, 108 to energy source 14 (FIG. 1A). For example, conductors 102, 106 may be embedded in elongated member 118, as shown in FIG. 2C, which is a conceptual cross-sectional view of elongated member 118 taken along plane 132 of FIG. 2A, plane 132 being perpendicular to longitudinal axis 116. As depicted, both conductor 102 and conductor 106 may be embedded within elongated member 118. Conductors 102, 106 may be fixed relative to elongated member 118, such that it may be difficult or impossible during normal operation of guidewire 112 to move embedded portions of conductors 102, 106 relative to elongated member 118 without damaging or destroying one of elongated member 118 and/or conductors 102, 106. Conductors 102, 106 may be embedded within elongated member 118 at a substantially static radial position within elongated member 118, such that conductors 102, 106 are embedded to extend substantially straight (e.g., parallel to longitudinal axis 116) within elongated member 118. By embedding conductors 102, 106 within elongated member 118, guidewire 112 may protect conductors 102, 106 from the external environment.

In other examples, one or both conductors 102, 106 may be configured to slide within elongated member 118 along a length (e.g., a proximal and/or medial length) of elongated member 118. For example, one or both conductors 102, 106 may have a lubricious outer surface and may be within a lumen that itself has a lubricious inner surface and extends partly along longitudinal axis 116 of elongated member 118. Such a lumen may only partially extend longitudinally along longitudinal axis 116 as a result of the lumen terminating at a proximal or medial or distal portion of elongated member 118 (such that conductors 102, 106 are embedded within elongated member 118 as discussed above distal to the lumen). Configuring one or both conductors 102, 106 such that one or both conductors 102, 106 may move somewhat within elongated member 118 along a length of elongated member 118 may improve a flexibility and therein a navigability of guidewire 112 as inserted into vasculature of the patient.

As discussed herein, conductors 102, 106 are configured to electrically couple electrodes 104, 108 to energy source 14 so that electrodes 104, 108 may deliver an electrical signal to fluid in contact with electrodes 104, 108 when electrodes 104, 108 are in blood vessel 60 of a patient. The electrical signal transmitted may form a corona, an electrical arc, a spark, or the like between a pair of adjacent and opposing coupled (e.g., one to a positive terminal and one to a negative terminal) electrodes 104, 108. FIG. 2D illustrates detail view 114 (from FIG. 2A) that depicts electrodes 104, 108 delivering an example electrical signal to fluid contacting electrodes 104, 108 coils of each of conductor 102, conductor 106, and spacing filars 110.

During the cavitation procedure, energy in the form of, for example, an electrical signal may be delivered to the fluid in blood vessel 60 and in contact with electrodes 104, 108 via electrodes 104, 108 to heat a portion of the fluid to generate steam/plasma bubbles 134 within the fluid. Bubbles 134 may represent relatively low-pressure pockets of vapor generated from the surrounding fluid. The low-pressure steam/plasma bubbles may eventually collapse in on themselves due to the relatively high pressure of the surrounding fluid and heat loss of the steam/plasma bubbles to the surrounding fluid. As bubbles 134 collapse, bubbles 134 release a relatively large amount of energy in the form of a high-energy pressure pulse wave 136 within fluid. In some examples, the formation and subsequent collapse of bubbles 134 may be short lived or nearly instantaneous, causing pressure pulse waves 136 to originate near electrodes 104, 108. The placement and direction of bubbles 134 and pulse waves 136 as depicted in FIG. 2D are for purposes of illustration only, as bubbles 134 and pulse waves 136 may be created at other locations and/or may define other trajectories in other examples.

The steam/plasma bubbles 134 may represent relatively low-pressure pockets of vapor sourced by the surrounding fluid of the vasculature. The low-pressure steam/plasma bubbles 134 eventually collapse in on themselves due to the relatively high pressure of the surrounding fluid of the vasculature and heat loss of the steam/plasma bubbles 134 to the surrounding fluid. As the steam/plasma bubbles collapse, bubbles 134 release a large amount of energy in the form of a high-energy pressure pulse wave 136 within fluid of the vasculature.

In some examples, the site for cavitation may be controlled by moving distal portion 122 that includes electrodes 104, 108, and/or controlling a subset of electrodes 104, 108 through which a signal is to be delivered to the fluid. For example, when applying corona-based cavitation, a subset of electrodes 104, 108 that define smaller surface areas (e.g., electrodes 104, 108 that define a surface area of less than 0.1 mm$^2$) may have a higher current density and therefore act as the site for cavitation to occur. Additionally, or alternatively, the direction of the resultant pressure pulse waves 136 produced by the cavitation may be controlled based on the circumferential orientation of respective electrodes 104, 108 where cavitation is to occur.

As described above, the formation and subsequent collapse of the steam/plasma bubbles 134 may be short lived or nearly instantaneous, causing the pressure pulse waves 136 to originate near respective primary or secondary of electrodes 104, 106 (e.g., where a primary electrode is coupled to a source of energy source 14 and a secondary electrode is coupled to a return of energy source 14). In some examples, the location where the steam/plasma bubbles 134 originate may be controlled by selecting a subset of electrodes 104, 108 that define a reduced amount of surface area that is exposed to fluid of the vasculature selected for cavitation. In certain examples, the steam/plasma bubbles 134 will originate on the associated electrode 104, 108 having the smallest exposed surface area. As such, guidewire 112 may be configured to include a selectable plurality of electrodes 104, 108 (such that when electrodes 104, 108 are selected those electrodes 104, 108 are then used to deliver a signal to fluid of the patient) that define a plurality of exposed surface areas to "steer" cavitation bubbles 134 and pulse waves 136. Energy source 14 may include processing circuitry (e.g., as described with respect to FIG. 11) configured to (automatically or with the aid of user input) select a subset of electrodes 104, 108 with which to deliver cavitation energy.

Once produced, pressure pulse waves 136 propagate through fluid of the vasculature where they impact the wall of blood vessel 60 within which distal portion 122 is deployed, transmitting the mechanical energy of pressure pulse wave 136 into the tissue of blood vessel 60 and lesion 64 at target site 62. The energy transmitted to lesion 64 may cause lesion 64 to become more radially pliable (e.g., as a result of lesion 64 fracturing or otherwise breaking apart). In some examples, the relative intensity of pressure pulse waves 136 may be adjusted by controlling the intensity of the electrical signal delivered between electrodes 104, 108. The intensity of the electrical signal may be a function of one or more of a voltage, a current, a frequency (e.g., a pulse rate in the case of pulses), a pulse width, or one or more other electrical signal parameters.

Figure 3:
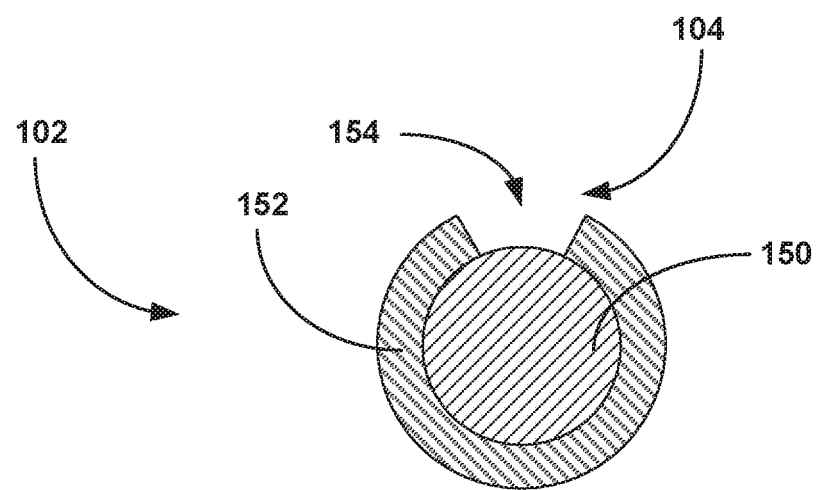
FIG. 3 is a schematic cross-sectional view of an aperture in an electrically insulative layer of the conductors of FIG. 2A defining an electrode, where the cross-section is taken perpendicular to a longitudinal axis of the guidewire.

Electrodes 104, 108 may be constructed or defined in any appropriate manner. In some examples, electrodes 104 and/or 108 may be defined by an exposed part of an electrically conducive portion of the respective conductor 102, 106. FIG. 3 is a conceptual cross-sectional view of an example conductor 102 that includes electrically conductive layer 150 (e.g., such as the electrically conductive materials described above), electrically insulative layer 152 (e.g., fluorinated ethylene propylene (FEP) or the like). Electrically insulative layer 152 defines aperture 154 that exposes electrically conductive layer 150 to define electrode 104. Aperture 154 may be relatively small. For example, aperture 154 may define a bore that extends substantially straight into conductor 102 and defines a generally circular shape that is approximately 0.01 mm to 0.05 mm in diameter, though aperture 154 may be other sizes and/or define other shapes in other examples. Electrically conductive layer 150 and electrically insulative layer 152 may extend longitudinally along substantially all of a length of conductor 102. While FIG. 3 is discussed with reference to conductor 102 and electrode 104, in some examples, the same constructions and techniques may be used on conductor 106 and electrode 108.

In some examples, as depicted, conductive layer 150 may be an electrically conductive core of conductor 102. Electrically insulative layer 152 may be an electrically insulative coating or an overmolded layer or the like. Conductor 102 may define aperture 154 to face an outer perimeter of guidewire 112 at the location of aperture 154. In some examples, aperture 154 may be created after conductors 102, 106 and spacing filars 110 are assembled/secured to shaft 124. For example, apertures 154 may be laser cut once conductors 102, 106 and spacing filars 110 are secured to shaft 124.

Figure 4:
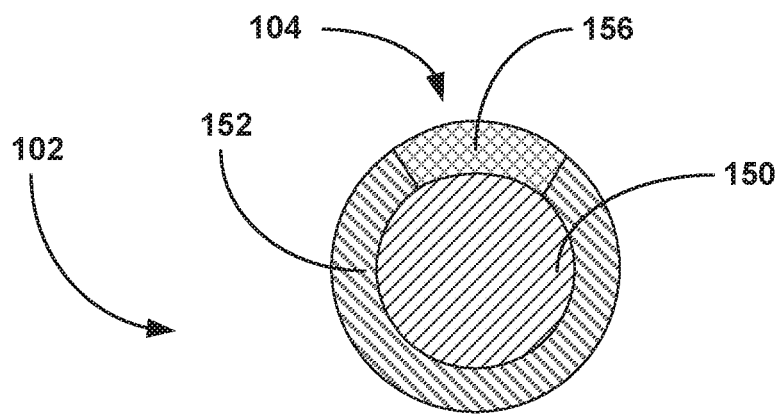
FIG. 4 is a schematic cross-sectional view of an electrode extending through an electrically insulative layer of the conductors of FIG. 2A and electrically coupled to an electrically conductive layer of the conductors, where the cross-section is taken perpendicular to a longitudinal axis of the guidewire.

FIG. 4 illustrates another example of one or more electrodes 104 of guidewire 112, and may also be representative of one or more electrodes 108. FIG. 4 is a conceptual cross-sectional view of conductor 102 that includes electrically conductive layer 150, electrically insulative layer 152, and electrically conductive element 156 coupled to electrically conductive layer 150 and extending radially out to an outer perimeter of conductor 102. Electrically conductive element 156 is positioned within aperture 154 and may, for example, fill aperture 154 to define a relatively continuous outer surface of conductor 102. Similar to FIG. 3, while FIG. 4 is discussed with reference to conductor 102 and electrode 104, in some examples, the same constructions and techniques may be used on conductor 106 and electrode 108. Conductive element 156 may be a discrete component that is secured to or otherwise formed on (e.g., deposited in aperture 154) conductor 102. Alternatively, conductive element 156 may be a portion of conductive layer 150 which extends out from electrically insulative layer 152 or is otherwise not enclosed by electrically insulative layer 152.

Figure 5A:
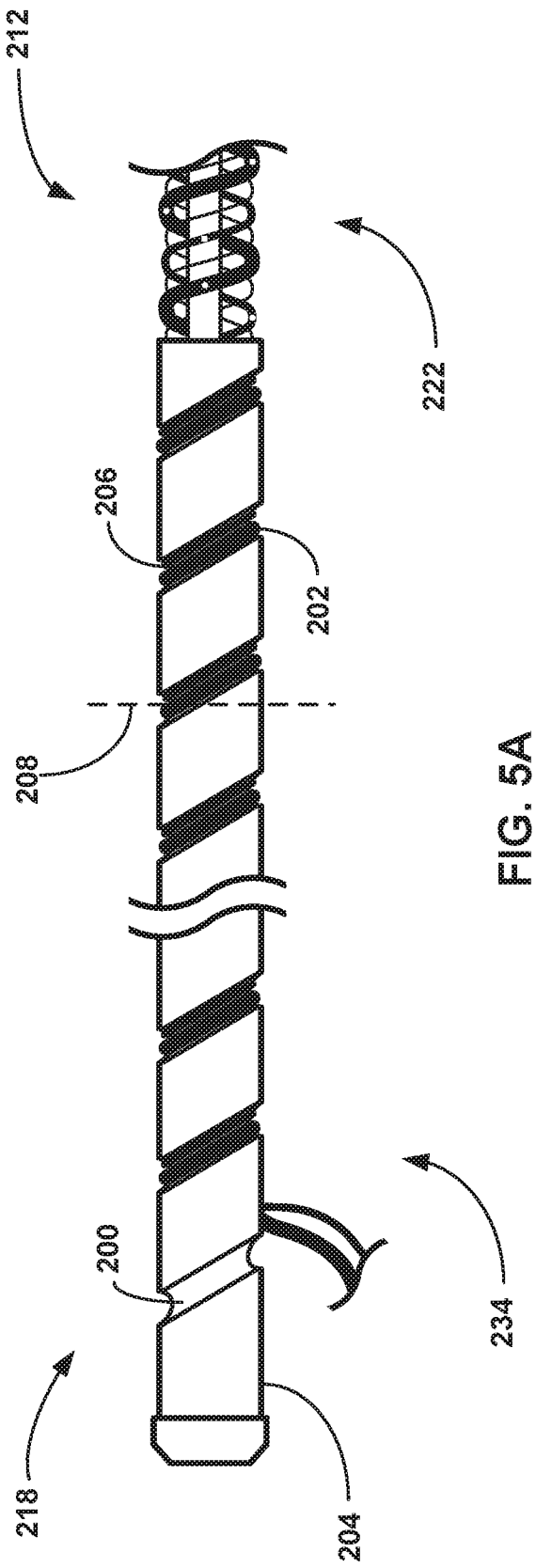
FIG. 5A is a schematic side view of conductors of an example guidewire extending around a perimeter of the guidewire within a recess defined by the guidewire.

In some examples, rather than being embedded in elongated member 118, one or both conductors of a guidewire may extend to a proximal portion of the guidewire along an outer perimeter of an elongated member of guidewire. For example, FIG. 5A is a conceptual side view of an example guidewire 212 that defines recess 200 in outer surface 204 of elongated member 218 in which conductors 202, 206 extend. Guidewire 212 may be substantially similar to guidewire 12 and guidewire 112, elongated member 218 may be substantially similar to elongated member 18 and elongated member 118, and conductors 202, 206 may be substantially similar to conductors 102, 106, respectively, with the exception of any differences described herein.

Figure 5C:
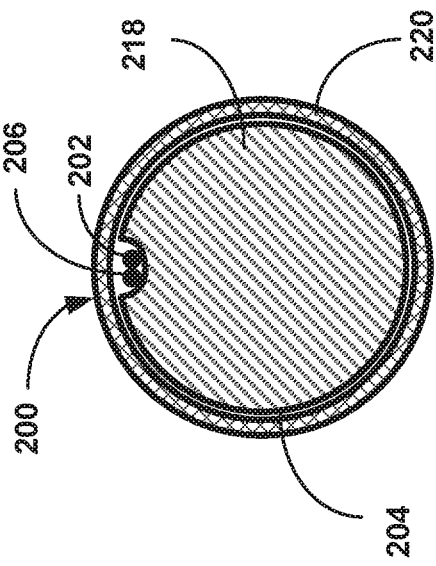
FIG. 5C is a schematic cross-sectional view of a sheath covering the elongated member and the conductors within the recess of the guidewire of FIG. 5A, where the cross-section is taken perpendicular to a longitudinal axis of the guidewire.
Figure 5B:
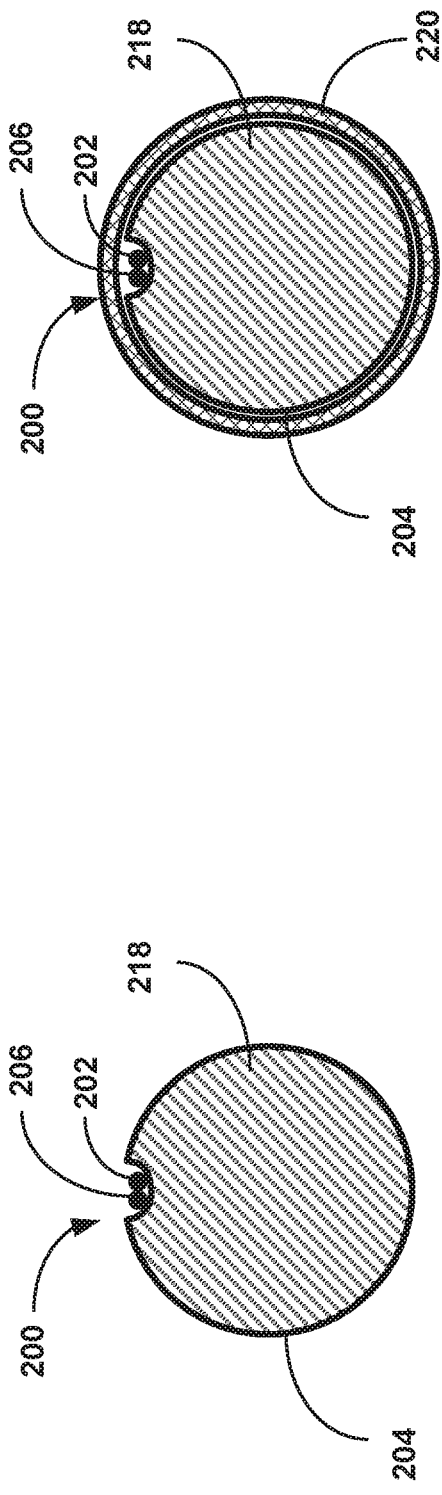
FIG. 5B is a schematic cross-sectional view of the conductors within the recess of the guidewire of FIG. 5A, where the cross-section is taken perpendicular to a longitudinal axis of the guidewire.

Recess 200 may extend radially into outer surface 204 of elongated member 218 and is configured to receive conductors 202, 206. As a result of recess 200 being configured to receive conductors 202, 206, elongated member 218 may be substantially solid throughout with substantially nothing embedded within and with no lumens or cavities (absent incidental cavities in the materials forming elongated member 218). In addition, positioning conductors 202, 206 in recess 200 rather than within an internal diameter of elongated member 218 may be enable elongated member 218 to be constructed with a smaller profile (e.g., outer diameter). FIG. 5B depicts a cross-sectional view of guidewire 212, recess 200, and conductors 202, 206 as taken along cut plane 208 of FIG. 5A, which is in a direction perpendicular to a longitudinal axis of guidewire 212. As depicted in FIG. 5B, elongated member 218 is a substantially solid member with no lumens or cavities as a result of recess 200.

Turning back to FIG. 5A, conductors 202, 206 may be positioned within recess 200 from distal portion 222 of guidewire 212 to a location adjacent a proximal end of guidewire 212. Recess 200 may circumferentially extend around an outer surface of elongated member 218 (e.g., to define a helix) as recess 200 extends longitudinally along guidewire 212. As a result of recess 200 defining a helix as recess 200 extends longitudinally along guidewire 212, recess 200 may more securely receive conductors 202, 206 than if recess 200 defined a relatively straight recess 200 that was substantially parallel to a longitudinal axis of guidewire 212. Put differently, as a result of conductors 202, 206 being configured to wrap around elongated member 218 when conductors 202, 206 are received within helical recess 200, conductors 202, 206 may have an improved radial securement to guidewire 212. In some examples, recess 200 may define a substantially static helical shape along elongated member 218, such that a pitch and an internal diameter of the helix defined by recess 200 does not change along a length of elongated member 218. In other examples, a pitch and/or an internal diameter of the helix defined by recess 200 may vary along a length of elongated member 218.

In some examples, conductors 202, 206 may be secured to recess 200 along an entire length of elongated member 218 or only part of elongated member 218. For example, conductors 202, 206 may be adhesively bonded or welded to a surface of recess 200. In some examples, conductors 202, 206 may be secured to recess 200 until conductors 202, 206 extend proximally to a proximal portion 234 of guidewire 212, at which point a proximal length of each conductor 202, 206 may be unsecured (e.g., unsecured to any component of guidewire 212). The unsecured proximal ends of conductors 202, 206 may then be electrically coupled to energy source 14 as described herein (e.g., directly coupled to energy source 14, or coupled to cables 36 that are coupled to energy source 14, or the like).

In certain examples, guidewire 212 may include an element that covers recess 200 once recess 200 receives conductors 202, 206 such that guidewire 212 defines a substantially uniform outer perimeter (e.g., rather than defining an exposed recess). For example, FIG. 5C depicts a cross-section of guidewire 212 along cut plane 208 of FIG. 5A once with sleeve 220 is placed over elongated member 218. Sleeve 220 may be placed over elongated member 218 once conductors 202, 206 are received by recess 200. Sleeve 220 may be a relatively thin longitudinal element that extends longitudinally over some, most, or all of a longitudinal length of recess 200. Sleeve 220 may be a film, a coating, an overmold, or the like. Sleeve 220 may serve to cover and protect conductors 202, 206 from the external environment. In some examples, sleeve 220 may secure conductors 202, 206 within recess 200 (e.g., in addition to or in lieu of the adhesive discussed above). Further, by defining a uniform outer perimeter, sleeve 220 may improve a navigability of guidewire 212 through patient (e.g., by eliminating features that may engage tissue of a patient during navigation).

Figure 6:
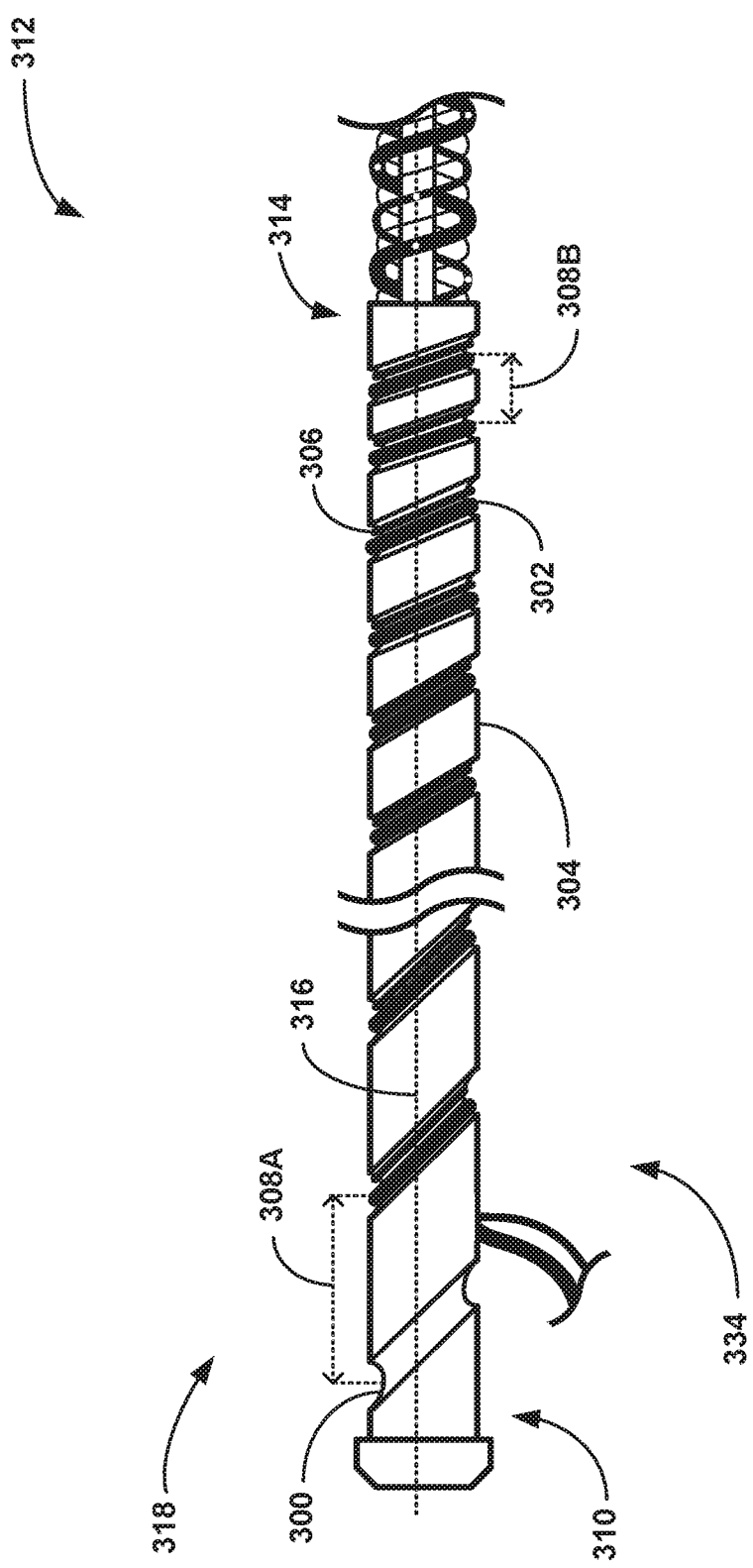
FIG. 6 is schematic side view of conductors of an example guidewire extending around a perimeter of the guidewire within a recess defined by the guidewire, the recess decreasing in pitch as the recess extends distally.

In some example, an elongated member of a guidewire may define a recess that itself defines a helix with a changing pitch. For example, FIG. 6 is a conceptual side-view of guidewire 312 that includes elongated member 318 that defines recess 300 in outer surface 304, where recess 300 is configured to receive conductors 302, 306. In contrast to recess 200 of FIG. 5, recess 300 defines different pitches 308A, 308B (collectively, "pitches 308") along length of elongated member 318. Guidewire 312 may be substantially similar to guidewires 12, 112, 212, elongated member 318 may be substantially similar to elongated members 18, 118, 218, and conductors 302, 306 may be substantially similar to conductors 102, 106, 202, 206, respectively, with the exception of any differences described herein.

Recess 300 defines a helix as recess 300 extends longitudinally along elongated member 318. For example, recess 300 may define helix as recess 300 extends along longitudinal axis 316 of guidewire 312. Elongated member 318 may define this helix to define a relatively larger pitch 308A near proximal end 310 of elongated member 318 and define a relatively smaller pitch 308B near distal end 314 of elongated member 318. Recess 300 may define pitches 308A, 308B (collectively, "pitches 308") to become gradually smaller as recess 300 extends distally. Put differently, recess 300 may define a helix that winds into tighter coils as the helix distally extends from proximal end 310 to distal end 314 of elongated member 318. As a result of recess 300 defining decreasing pitches 308 as recess 300 extends distally, elongated member 318 may get more flexible (as a result of more material being removed from elongated member 318) as elongated member 318 extends distally, which may facilitate navigation of guidewire 312 through blood vessel 60 of a patient.

In some examples, multiple conductors may be positioned in the same recess. In other examples, however, an elongated member of a guidewire may define multiple recesses, each recess being configured to receive respective one or more conductors. FIG. 7A is a conceptual side-view of an example guidewire 412 that includes elongated member 418 that defines two recesses 400A, 400B (collectively, "recesses 400"), where each recess 400A, 400B is configured to receive a respective one of conductors 402, 406. Guidewire 412 may be substantially similar to guidewires 12, 112, 212, or 312, elongated member 418 may be substantially similar to elongated members 18, 118, 218, or 318, conductor 402 may be substantially similar to conductors 102, 106, 202, 206, 302, or 306, and recess 400 may be substantially similar to recess 200 or 300, respectively, with the exception of any differences described herein.

Elongated member 418 may define first recess 400A configured to receive first conductor 402 and define second recess 400B configured to receive second conductor 406. Recesses 400 may both define respective helices as recesses 400 extend longitudinally along elongated member 418. In some examples, recesses 400 may define substantially similar helices. For example, helices as defined by recesses 400 may define substantially similar pitches and may extend a similar radial distance into outer surface 404 of elongated member 418 toward longitudinal axis 416 of guidewire 412. In other examples, first recess 400A may define a different helix than second recess 400B, such that first recess 400A defines a different pitch or extends radially into outer surface 404 of elongated member 418 more or less than second recess 400B.

In certain examples, recesses 400 may distally terminate at a circumferential location that enables a respective conductor 402, 406 to not alter a pitch as the respective conductor 402, 406 coils around shaft 424. For example, as depicted in FIG. 7A, recess 400A that receives conductor 406 distally terminates at distal end 414 of elongated member 418 at a position that enables conductor 406 to continue coiling around shaft 424 in a substantially similar manner as how conductor 406 was coiling within recess 400A. Thus, recesses 400 may be configured to enable conductors 402, 406 to define respective helices that have substantially static pitches and internal diameters on elongated member 418, around shaft 424, and at the transition therebetween.

In order for recesses 400 to enables conductors 402, 406 to define such static helices across distal end 414 of elongated member 418, recesses 400 may be located 180° separated across from each other on elongated member 418. For example, FIG. 7B depicts cross-sectional view of elongated member 418 as taken along cut plane 418 of FIG. 7A. As depicted, recess 400A as receiving conductor 406 is 180° away from recess 400B as receiving conductor 402. In other examples where helices are defined differently, recesses 400 may be separated by an amount other than 180°.

Figure 8A:
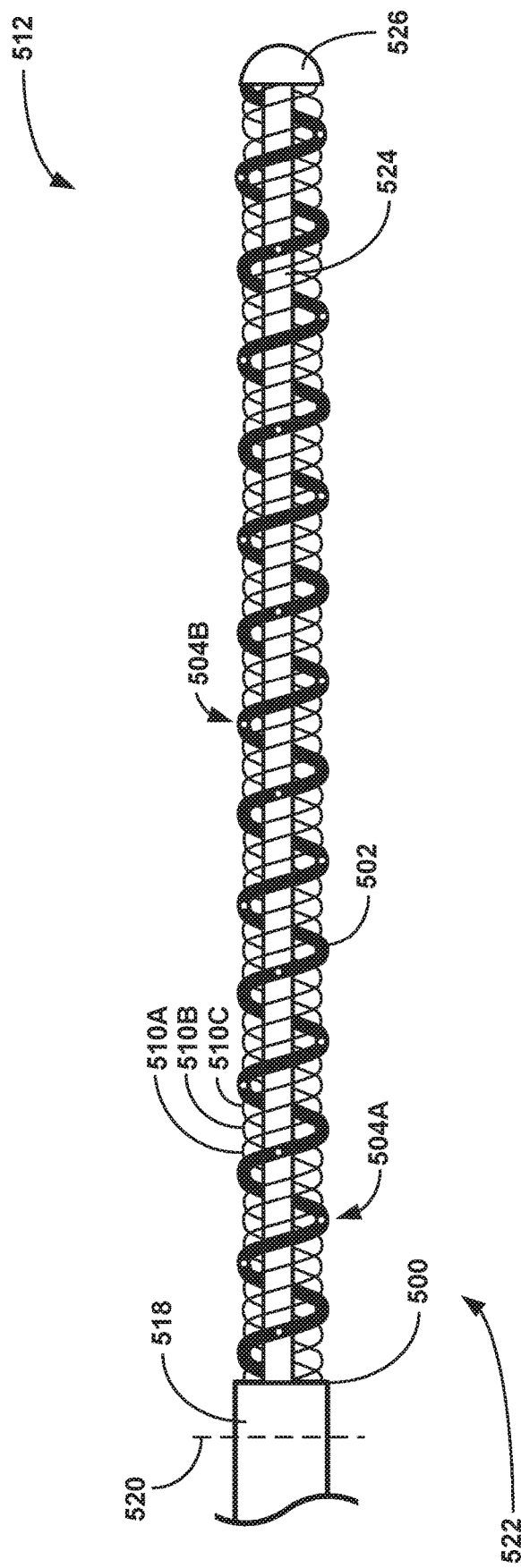
FIG. 8A is a schematic side view of an example guidewire that includes a conductor and a plurality of spacing filars extending around an electrically conductive shaft at a distal portion of the guidewire as well as a plurality of electrodes defined by or coupled to the conductor adjacent the shaft.

In some examples, a guidewire may only include one conductor coiling around an electrically conductive shaft at a distal portion of the guidewire. FIG. 8A is a conceptual side view of an example guidewire 512 that includes distal portion 522 extending distally from elongated member 518 and spacing filars 510A-510C (collectively, "spacing filars 510) coiling around shaft 524. Distal portion 522 includes conductor 502. Conductor 502 and spacing filars 510 may coil around shaft 524 between elongated member 518 and distal tip 526. Guidewire 512 may be substantially similar to guidewires 12, 112, 212, 312, and/or 412, elongated member 518 may be substantially similar to elongated members 18, 118, 218, 318, and/or 418, conductor 502 may be substantially similar to conductors 102, 106, 202, 206, 302, 306, 402, and/or 406, shaft 524 may be substantially similar to shafts 24 and/or 124, spacing filars 510 may be substantially similar to spacing filars 110, and distal tip 526 may be substantially similar to distal tip 26 and/or 126, respectively, with the exception of any differences described herein.

As depicted in FIG. 8A, conductor 502 and three spacing filars 510 may coil around shaft 524. In other examples, guidewire 512 may include a greater or a fewer number of spacing filars 510. Spacing filars 510 may be configured to define a pitch of conductor 502. Distal portion 522 of guidewire may further include a plurality of electrodes 504A, 504B (collectively, "electrodes 504"). Guidewire 512 may include electrodes 504 at a plurality of longitudinal locations and/or a plurality of circumferential locations. Conductor 502 may be configured to electrically couple electrodes 504 to energy source 14. For example, conductor 502 may be configured to couple electrodes to a positive or supply terminal of a cavitation energy source 14. Electrodes 504 may be configured to be exposed to a fluid of blood vessel 60 of a patient when distal portion 522 of guidewire 512 is navigated to target site 62.

In some examples, conductor 502 may include an electrically conductive layer. The electrically conductive layer may be at least partially covered with a material with electrically insulating properties. Conductor 502 may define some or all electrodes 504 through a series of apertures in an electrically insulating layer that exposes the electrically conductive layer of conductor 502 (e.g., similar to FIG. 3). Alternatively, or additionally, electrodes 504 may include discrete physical components that are physically connected to conductor 502 and electrically coupled to the electrically conductive layer of conductor 502 through the electrically insulative layer (e.g., similar to FIG. 4).

In the example shown in FIG. 8A, shaft 524 of guidewire 512 defines or carries a second electrode of guidewire 512. For example, shaft 524 may include an electrically conductive material as described herein. In some examples, shaft 524 includes be a solid shaft comprised substantially entirely of the electrically conductive material. In other examples, shaft 524 may contain an inner electrically conductive core and an electrically-insulative outer layer, such that apertures through the electrically insulative layer define electrodes of shaft 524. Shaft 524 may be electrically coupled to energy source 14. For example, shaft 524 may extend within elongated member 518 to a proximal end of guidewire 512 and may be configured to be electrically coupled to a ground or negative terminal of energy source 14 (e.g., through a wire such as one of cables 36 that is coupled to shaft 524 through hub 32 and configured to be coupled to energy source 14). An outer surface of shaft 524 may be configured to be exposed to a fluid of a patient when guidewire 512 is navigated to target site 62 in a patient. In this way, electrodes 504 of/on conductor 502 and shaft 524 may be used to deliver an electrical signal to a fluid in contact with both the respective electrode 504 and an adjacent portion of shaft 524 to cause the fluid to undergo cavitation to generate a pressure pulse wave within the fluid.

Figure 8C:
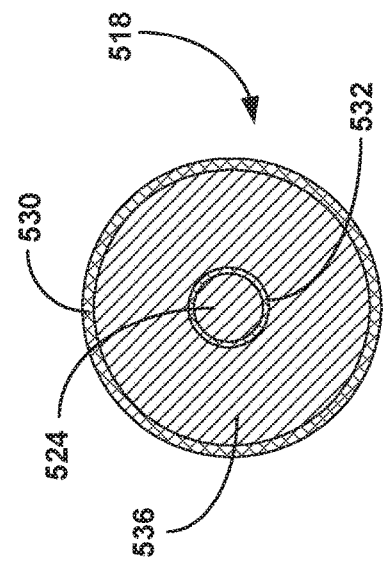
FIG. 8C is an example cross-sectional view of the guidewire of FIG. 8A, where the cross-section is taken perpendicular to a longitudinal axis of the guidewire.
Figure 8B:
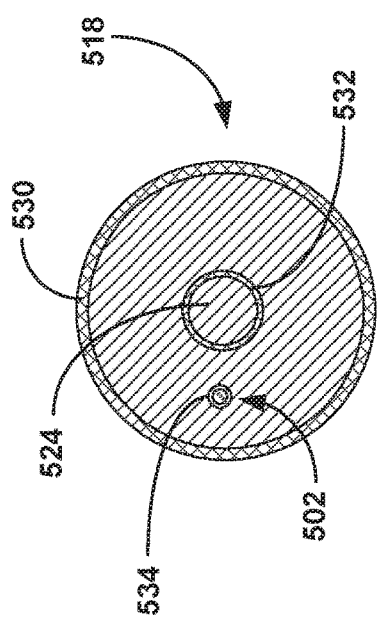
FIG. 8B is an example cross-sectional view of the guidewire of FIG. 8A and illustrates electrically insulative layers around a hypotube and an electrically conductive shaft as well as the conductor embedded in the hypotube, where the cross-section is taken perpendicular to a longitudinal axis of the guidewire.

Shaft 524 and conductor 502 may both be coupled to respective conductive elements that extends longitudinally to a proximal portion of guidewire 512. For example, FIG. 8B is an example conceptual cross-sectional view taken from cut-plane 520 of guidewire 512, cut-plane 520 being perpendicular to a longitudinal axis of guidewire 512. In the example depicted in FIG. 8B, both shaft 524 and conductor 502 are embedded within elongated member 518. Elongated member 518 include one or more electrically insulative layers and/or coatings to maintain electrical insulation between shaft 524 and conductor 502 as both extend through elongated member 518. For example, elongated member 518 may include outer electrically insulative layer 530 around an outer perimeter of elongated member 518 as well as an inner electrically insulative layer 532 around an outer perimeter of shaft 524. Additionally, or alternatively, conductor 502 may include electrically insulative layer 534 around an outer perimeter of conductor 502. This construction may remain substantially constant throughout a length of elongated member 518, such that conductor 502 and shaft 524 always have electrically insulative layers between respective conductive layers.

In other examples, conductor 502 may not extend into elongated member 518, but may instead be electrically coupled to an electrically conductive layer of elongated member 518. For example, FIG. 8C is another example conceptual cross-sectional view taken from cut-plane 520 of guidewire 512. As depicted in FIG. 8C, elongated member 518 may include electrically conductive shaft 524 and electrically insulative layer 532 around an outer perimeter of shaft 524. Elongated member 518 may further include electrically conductive layer 536. Outer electrically insulative layer 530 may cover an outer perimeter of electrically conductive layer 536. Electrically conductive layer 536 of elongated member 518 may be electrically coupled to conductor 502 at distal end 500 of elongated member 518. Both electrically conductive layer 536 and shaft 524 may to a proximal portion of guidewire 512, at which location both may be electrically coupled to energy source 14 as described herein (e.g., with cables 36 that couple through hub 32 to conductive layer 536 and shaft 524 as partially depicted in FIG. 1A).

A cross-sectional construction of elongated member 518 as depicted in FIG. 8C (and FIG. 8B, as discussed above) may be relatively consistent throughout a length of elongated member 518 (e.g., such that respective elements are electrically insulated from each other and from blood vessel 60 of a patient), though in some examples elongated member 518 may get thinner or otherwise get constructed to be relatively more flexible as elongated member 518 extends distally. For example, outer electrically insulative layer 530 may get relatively thicker while conductive layer 536 gets relatively smaller (e.g., such that an overall diameter of elongated member 518 remains substantially static) as elongated member 518 extends distally, such that a flexibility of elongated member 518 increases towards a distal end of elongated member 518.

Figure 9:
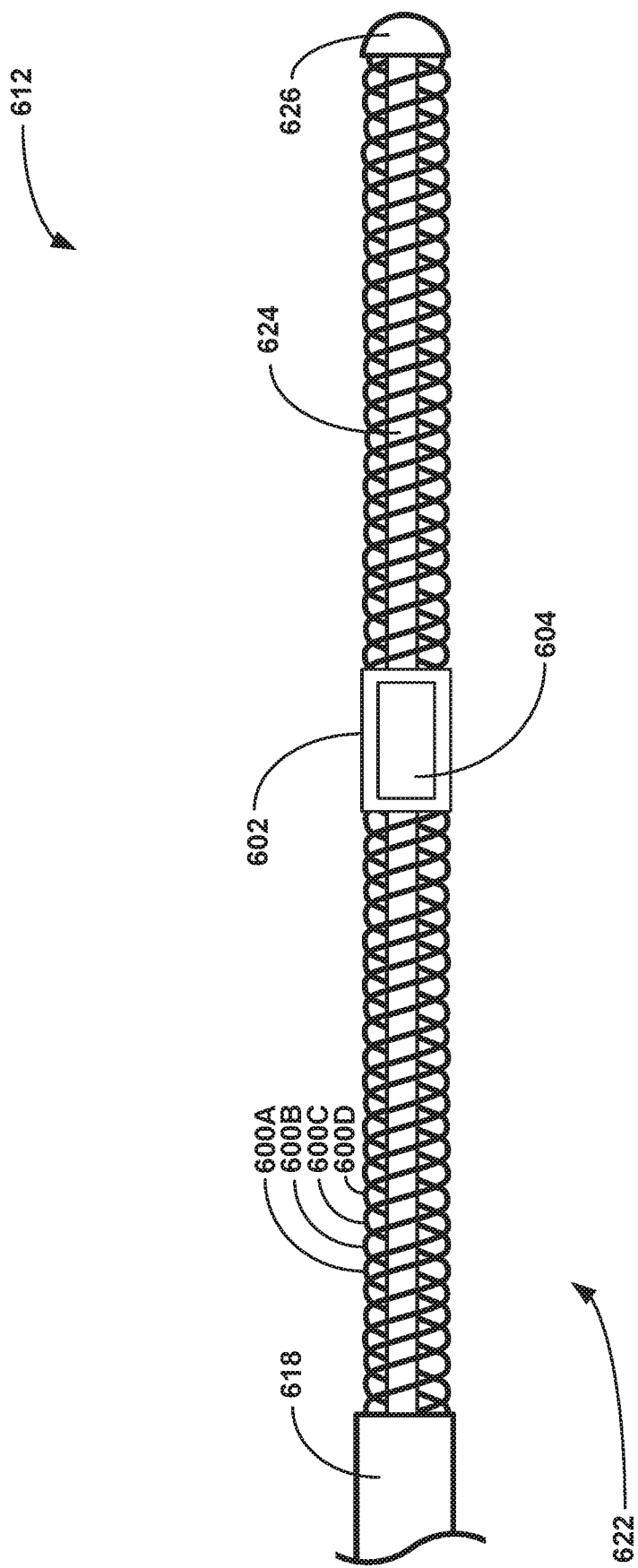
FIG. 9 is a schematic side view of an example guidewire that includes a hypotube transitioning into a multi-filar coil that extends around an electrically conductive shaft at a distal portion of the guidewire as well as a marker band electrode coupled to the multi-filar coil adjacent the shaft.

In some examples, a guidewire may include a distal portion where an electrode is not defined by a coil element or otherwise coupled to a guidewire at a discrete radial position, but is instead a discrete element that extends around most or all of the circumference of the shaft. FIG. 9 is a conceptual side view of a part of an example guidewire 612 that includes distal portion 622 with electrically conductive coils 600A-600D (collectively, "conductive coils 600") coiling around shaft 624 and coupled to marker band electrode 602 that extends around (e.g., encircles) shaft 624. Marker band electrode 602 may be comprise of any suitable materials, such as biocompatible materials. For example, marker band electrode 602 may include platinum and gold. In some examples, marker band electrode 602 may define conductive surface 604 that is exposed to a fluid of vasculature and extends out in one general radial direction (e.g., rather than conductive surface 604 fully surrounding shaft 624). Where marker band electrode 602 defines conductive surface 604 that extends out in one general direction from shaft 624, a clinician may rotate guidewire 212 during cavitation to achieve 360° of treatment within blood vessel 60.

Conductive coils 600 may coil around shaft 624 between elongated member 618 and distal tip 626. Guidewire 612 may be substantially similar to guidewires 12, 112, 212, 312, 412, and/or 512, elongated member 618 may be substantially similar to elongated members 18, 118, 218, 318, 418, and/or 518, conductive coils 600 may be substantially similar to one or both of conductors 102, 106, 202, 206, 302, 306, 402, 406, 502, and/or 506, shaft 624 may be substantially similar to shafts 24, 124, 424, and/or 524, and distal tip 626 may be substantially similar to distal tip 26, 126, and/or 526, respectively, with the exception of any differences described herein.

Conductive coils 600 may be coupled to an electrically conductive layer or portion of elongated member 618. For example, elongated member 618 may include an electrically conductive layer of a hypotube or the like (e.g., similar to conductive layer 536 of FIG. 8C) that is electrically coupled to conductive coils 600. In some examples, a hypotube of elongated member 618 may be formed or cut to extend out to define conductive coils 600 coiling around shaft 624 of distal portion 622. One or some or all of conductive coils 600 may be configured to couple to marker band electrode 602 or respective one or more marker band electrodes. Marker band electrode 602 may be fixedly secured to conductive coils 600. For example, conductive coils 600 may be extend distally from elongated member 618 to distal tip 626, such that marker band electrode 602 is secured to an outer perimeter of conductive coils 600. Though only one marker band electrode 602 is shown in distal portion 622 for purposes of illustration, in some examples, distal portion 622 may include a plurality of marker band electrodes 602 coupled to and/or supported by conductive coils 600.

In some examples, conductive coils 600 may include an electrically insulative material along an outer surface of conductive coils 600. For example, conductive coils 600 may include an outer layer of an electrically insulating material (e.g., such as polytetrafluoroethylene (PTFE)), or conductive coils 600 may receive an electrically insulating coating. The electrically insulative material of conductive coils 600 may be configured to electrically insulate conductive coils 600 from fluid of blood vessel 60 or a patient, to ensure that the electrical signal is transmitted to fluid from market band electrode 602 and not conductive coils 600.

Shaft 624 of guidewire 612 may include a second electrode. For example, shaft 624 may include conductive material (e.g., at least along an outer surface of shaft 624). Shaft 624 may be electrically coupled to energy source 14, similar to shaft 524 of guidewire 512. For example, shaft 624 may be coupled to a ground or negative terminal of energy source 14. An outer surface of shaft 624 may be configured to be exposed to a fluid of a patient when guidewire 612 is navigated to target site 62 in a patient. In this way, marker band electrode 602 and shaft 624 may be used to deliver an electrical signal to a fluid in contact with both marker band electrode 602 and an adjacent portion of shaft 624 to cause the fluid to undergo cavitation to generate a pressure pulse wave within the fluid.

Figure 10A:
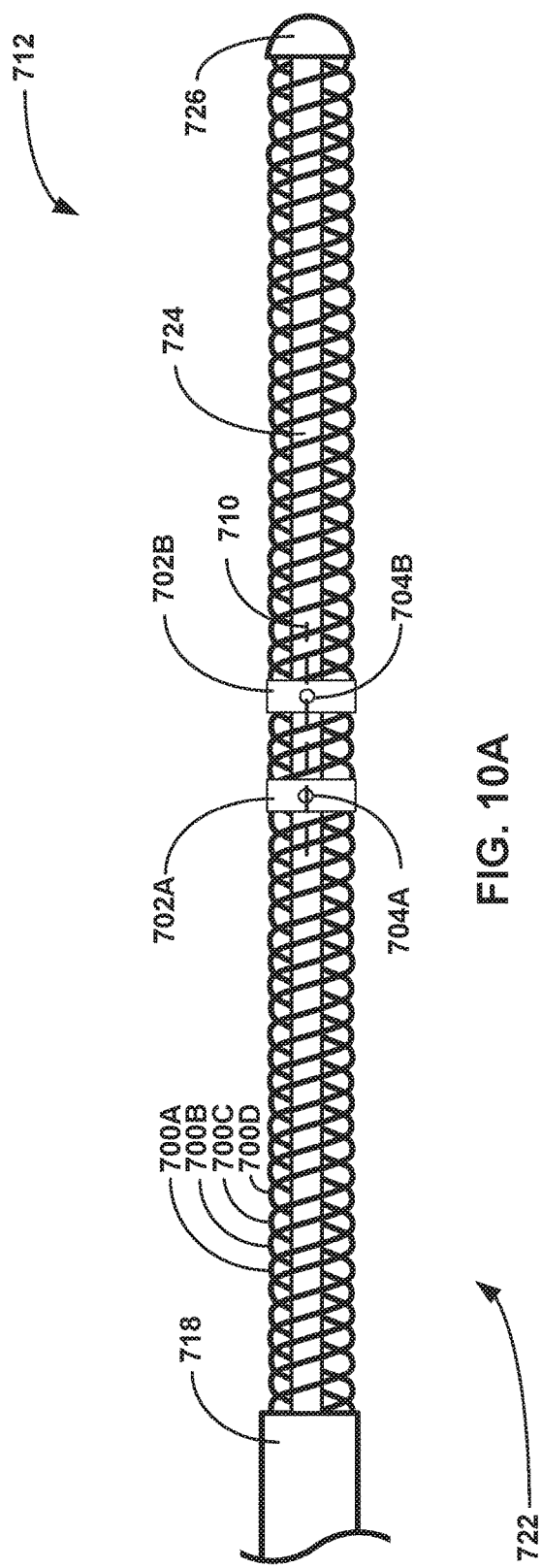
FIG. 10A is a schematic side view of an example guidewire that includes a hypotube transitioning into a multi-filar coil around an electrically conductive shaft at a distal portion of the guidewire as well as bands coupled to the shaft defining a plurality electrodes.

In some examples, a marker band electrode may define an aperture that extends to an electrically conductive shaft to define the electrode. For example, FIG. 10A is a conceptual side view of an example guidewire 712 that includes distal portion 722 with conductive coils 700A-700D (collectively, "conductive coils 700") coiling around shaft 724 and coupled to marker band electrodes 702A, 702B (collectively, "marker band electrodes 702") that define apertures 704A, 704B (collectively, "apertures 704") and encircle shaft 724. Conductive coils 700 may coil around shaft 724 between elongated member 718 and distal tip 726. Guidewire 712 may be substantially similar to guidewires 12, 112, 212, 312, 412, 512, and/or guidewire 612, elongated member 718 may be substantially similar to elongated members 18, 118, 218, 318, 418, 518, and/or 618, conductive coils 700 may be substantially similar to conductors 102, 106, 202, 206, 302, 306, 402, 406, 502, 506, and/or conductive coils 600, shaft 724 may be substantially similar to shafts 24, 124, 424, 524, and/or 624, and distal tip 726 may be substantially similar to distal tip 26, 126, 526, and/or 626, respectively, with the exception of any differences described herein.

Similar to guidewire 612, conductive coils 700 of guidewire 712 may be coupled to an electrically conductive layer or portion of elongated member 718. For example, elongated member 718 may define an electrically conductive hypotube or the like (e.g., similar to conductive layer 536 of FIG. 8C) that is electrically coupled to conductive coils 700. Further, similar to guidewire 612, a hypotube of elongated member 718 may extend out to define conductive coils 700 coiling around shaft 724 of distal portion 722. One or some or all of conductive coils 700 may be configured to electrically couple to respective marker band electrodes 702.

Figure 10B:
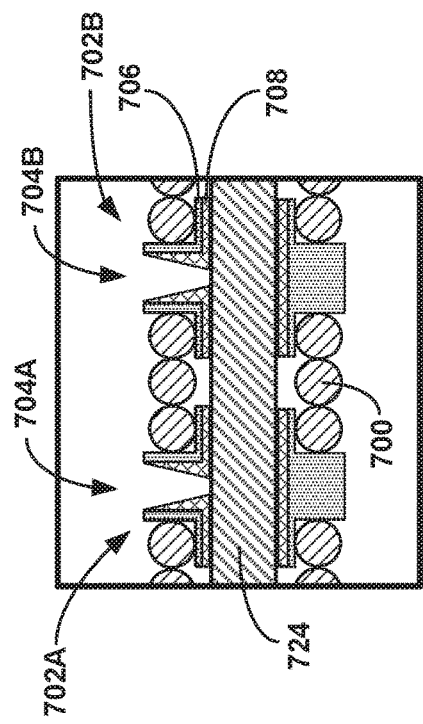
FIG. 10B is a schematic cross-sectional view of the guidewire of FIG. 10A and illustrates a band defining an aperture extending from the electrically conductive shaft to an outer perimeter of the guidewire, where the cross-section is taken along a longitudinal axis of the guidewire.

Marker band electrodes 702 may be secured to shaft 724 and/or conductive coils 700. For example, FIG. 10B is a conceptual cross-sectional view taken along cut-plane 710 of FIG. 10A of marker band electrodes 702. As depicted, marker band electrodes 702 may define a face that rests against shaft 724. The face of marker band electrodes 702 be welded or adhered or the like to shaft 724. Similarly, conductive coils 700 may be secured (welded or adhered or the like) to another face of marker band electrodes 702. Conductive coils 700 may be secured to marker band electrodes 702 in such a way that conductive coils 700 are electrically coupled to marker band electrodes 702.

Shaft 724 of guidewire 712 may be a second electrode similar to shaft 624 of guidewire 612. For example, shaft 724 may include conductive material such as is described herein (that is configured to be electrically coupled to energy source 14 according to the techniques described herein. Marker band electrodes 702 may define apertures 704 that expose conductive material of shaft 724 to fluid of blood vessel 60. In some examples, shaft 724 may be coated or otherwise covered with an electrically insulative material outside of areas exposed by apertures 704, such that conductive material of shaft 724 that is coupled to energy source 14 is only exposed to fluid of blood vessel 60 at apertures 704.

Marker band electrodes 702 may define conductive outer layer 706 and electrically insulative inner layer 708. Conductive outer layer 706 may be configured to be electrically coupled to conductive coils 700 and therein coupled to one terminal of energy source 14, and shaft 724 may be coupled to the opposing terminal of energy source 14. Marker band electrodes 702 may define apertures 704 of any suitable size and shape (e.g., hole or ring) that passes through conductive outer layer 706 and electrically insulative layer 708 to provide fluid communication between conductive outer layer 706 and shaft 724 (e.g., via fluid of blood vessel 60). Layers 706, 708 of marker band electrodes 702 may have any suitable dimension. In some examples, each of marker band electrodes 702 may comprise a ring or cylindrical body that defines a longitudinal length (measured along a longitudinal axis of guidewire 712) of about 1 mm. During the cavitation procedure, an electrical signal may be delivered between conductive outer layer 706 and shaft 724 using fluid of blood vessel 60 within apertures 704. The electrical signal transmitted may form a corona, an electrical arc, a spark, or the like between conductive outer layer 706 and shaft 724 using the fluid within apertures 704 as an electrically conductive media to cause the fluid to undergo cavitation.

Figure 11:
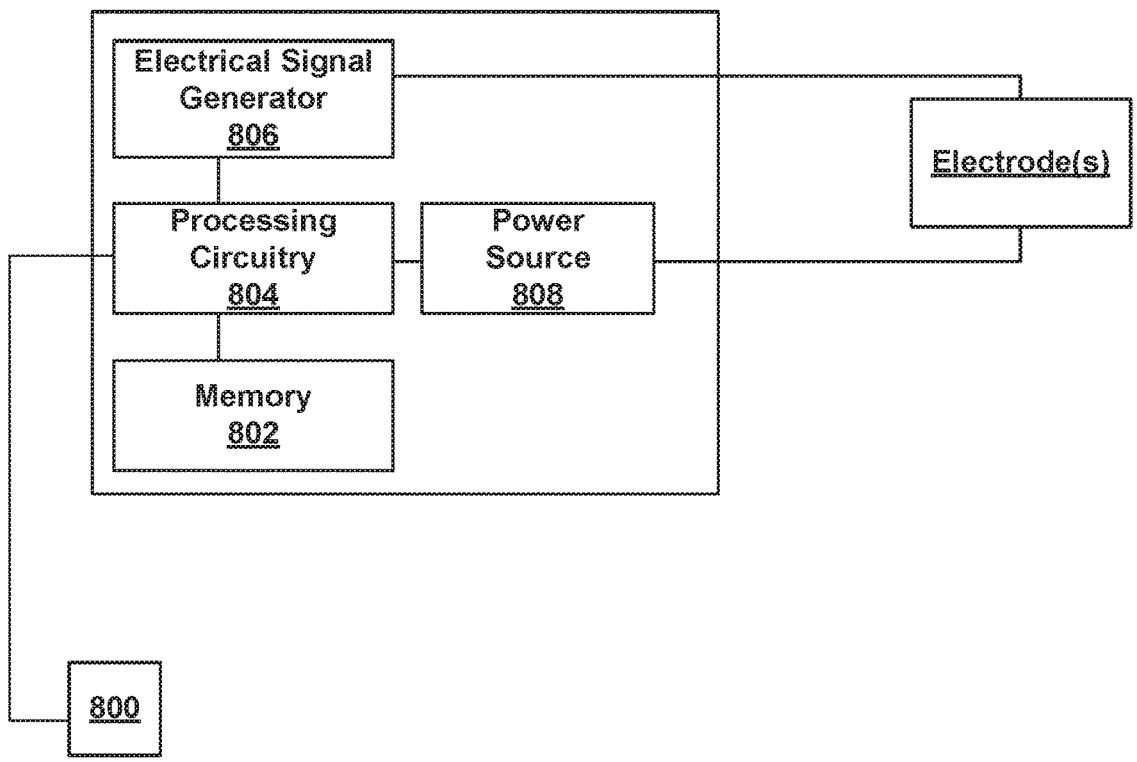
FIG. 11 is a schematic block diagram of an example cavitation energy source that may be used with the guidewire of FIG. 1 to induce cavitation within a fluid

FIG. 11 shows a schematic block diagram of an example energy source 14 that may be used with any of the guidewires discussed herein (e.g., guidewire 12, 112, 212, 312, 412, 512, 612, 712) to induce cavitation within a fluid of blood vessel 60 of a patient using electrodes of the guidewires discussed herein (e.g., electrodes 30, 104, 108, 504, 524, 602, 624, 704, 724). However, for purposes of illustration and brevity, energy source 14 is primarily discussed in relation to guidewire 12 and electrodes 30. Energy source 14 includes control mechanism 800, memory 802, processing circuitry 804, electrical signal generator 806, and power source 808.

Processing circuitry 804 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 804. The functions attributed to processors described herein, including processing circuitry 804, may be provided by a hardware device and embodied as software, firmware, hardware, or any combination thereof. In some examples, processing circuitry 804 may include instructions to recognize a particular electrode 30 configuration or allow a clinician to manually input the specific electrode 30 configuration of guidewire 12. In some examples, energy source 14 may include additional components such as, a display device or user input device that are not expressly shown for displaying information from processing circuitry 804 or allowing the clinician to input information.

Memory 802 may include any volatile or non-volatile media, such as a random access memory (RAM), read only memory (ROM), non-volatile RAM (NVRAM), electrically erasable programmable ROM (EEPROM), flash memory, and the like. Memory 802 may store computer-readable instructions that, when executed by processing circuitry 804, cause processing circuitry 804 to perform various functions described herein. Memory 802 may be considered, in some examples, a non-transitory computer-readable storage medium including instructions that cause one or more processors, such as, e.g., processing circuitry 804, to implement one or more of the example techniques described in this disclosure. The term "non-transitory" may indicate that the storage medium is not embodied in a carrier wave or a propagated signal. However, the term "non-transitory" should not be interpreted to mean that memory 802 is non-movable. As one example, memory 802 may be removed from energy source 14, and moved to another device. In certain examples, a non-transitory storage medium may store data that can, over time, change (e.g., in RAM).

Processing circuitry 804 is configured to control energy source 14 and electrical signal generator 806 to generate and deliver the electrical signal across one or more electrodes 30 to induce cavitation of a fluid of a patient. Electrical signal generator 806 includes electrical signal generation circuitry and is configured to generate and deliver an electrical signal in the form of pulses and/or a continuous wave electrical signal. In the case of electrical pulses, electrical signal generator 806 may be configured to generate and deliver pulses having an amplitude of about 500 volts (V) to about 4000 V (e.g., about about 1500V to about 3000 V), a pulse width of about 1 microsecond to about 5 microseconds, and a frequency of about 0.5 Hertz (Hz) to about 5 Hz. In some examples, guidewire 12 may be configured such that conductors as described herein are independently coupled to one or more electrodes 30. In such examples, processing circuitry 804 may control electrical signal generator 806 to generate and deliver multiple electrical signals via different combinations of conductors and/or electrodes 30. In these examples, energy source 14 may include a switching circuitry to switch the delivery of the electrical signal using electrodes 30, e.g., in response to control by processing circuitry 804.

Power source 808 delivers operating power to various components of energy source 14. In some examples, power source 808 may represent hard-wired electrical supply of alternating or direct electrical current. In other examples, power source 808 may include a small rechargeable or non-rechargeable battery and a power generation circuit to produce the operating power. Recharging may be accomplished through proximal inductive interaction between an external charger and an inductive charging coil within energy source 14.

A control mechanism 800 (e.g., a foot pedal, handheld device, or remote-control device) may be connected to energy source 14 to allow the clinician to initiate, terminate, and/or adjust various operational characteristics of energy source 14. For example, control mechanism 800 may configured to initiate, terminate, and/or adjust power delivery as provided by energy source 14. Control mechanism 800 may be positioned in a sterile field and operably coupled to the energy source 14. Control mechanism 800 may be configured to enable the clinician to selectively activate and deactivate the energy delivered to one or more electrodes 30. In other embodiments, control mechanism 800 may be built into hub 32 of guidewire 12.

Figure 12:
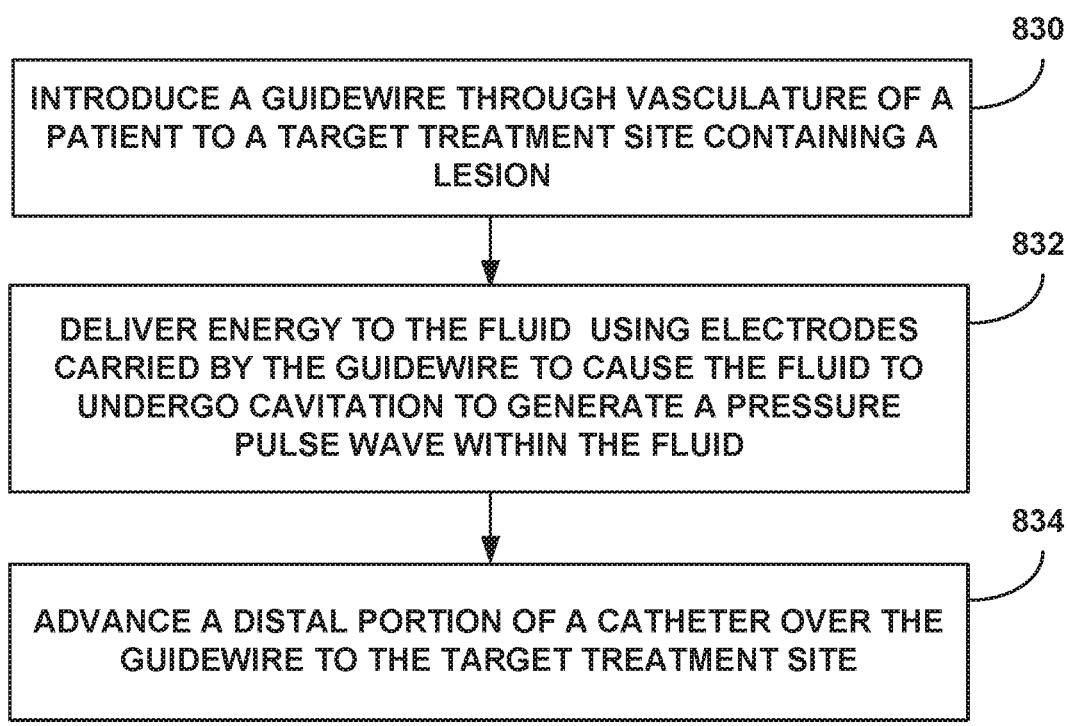
FIG. 12 is a flow diagram of an example technique of using example guidewires described herein.

FIG. 12 is a flow diagram of an example technique of using guidewires described herein. For illustrative purposes, the techniques of FIG. 12 are described with reference to the various aspects of guidewire 12, however, such descriptions are not intended to be limiting and the techniques of FIG. 12 may be used with other guidewires or guidewires 12 and guidewires 12 may be used in other applications. The technique of FIG. 12 includes introducing a guidewire 12 through blood vessel 60 of a patient and guiding a distal portion 22 of guidewire 12 to target site 62 adjacent to lesion 64 (830). Guidewire 12 may be configured to be navigated to a plurality of target sites 62. For example, guidewire 12 may be navigated to a target site that defines a relatively small amount of clearance (e.g., less than 0.5 mm of clearance).

The technique of FIG. 12 also includes controlling energy source 14 to deliver energy to a fluid within blood vessel 60 of a patient using electrodes 30 having at least one surface exposed to fluid to cause the fluid to undergo cavitation to generate a pressure pulse wave within fluid (832). As described above, electrode 30 may transmit energy to fluid (e.g., electrical energy) that rapidly heats a portion of fluid to produce short-lived gaseous steam/plasma bubbles within fluid. The steam/plasma bubbles may represent relatively low-pressure pockets of vapor generated from the surrounding fluid. The low-pressure steam/plasma bubbles eventually collapse in on themselves due to the relatively high pressure of the surrounding fluid. As steam/plasma bubbles collapse, the bubbles release a large amount of energy in the form of a high-energy pressure pulse wave within fluid that propagate through fluid where they impact the wall of blood vessel 60 transmitting the mechanical energy of the pressure pulse wave into the tissue of blood vessel 60 and lesion 64. The energy transmitted to lesion 64 may cause lesion 64 to fracture or beak apart.

In some examples, the electrical energy delivered to fluid via electrodes 30 may be in the form of a corona, an electrical arc, a spark or the like. The electrical signal may be a continuous wave signal or in the form of a plurality of pulses, and may have any suitable electrical signal parameters for creating the cavitation. For example, the electrical signal may have an amplitude of about 500 volts (V) to about 5000 V (e.g., about 1500V to about 3000 V), a pulse width of about 1 microsecond (µs) to about 5 µs for arc-type cavitation or about 10 µs to about 200 µs for corona-type cavitation, and a frequency of about 0.5 Hertz (Hz) to about 1000 Hz.

In some examples, catheter 38 may be advanced over guidewire 12 (834). Catheter 38 may include balloon 44 on distal end 40 of catheter 38. A port at distal end 40 of catheter 38 may receive proximal portion 34 of guidewire 12. Catheter 38 may be advanced over guidewire 12 until distal portion 42 of catheter 38 is adjacent lesion 64. A clinician may be able to navigate distal portion 42 to lesion 64 as a result of guidewire 12 fracturing lesion 64 as described above. Balloon 44 may be inflated to open-up blood vessel 60 of the patient, restoring blood vessel 60 to a normal or larger flow diameter. Additionally, or alternatively, this cavitation treatment of lesion 64 may be used in conjunction with a stent to restore blood vessel 60 to a normal or larger flow diameter or delivery of a prosthetic heart valve to a native heart valve location. After the cavitation procedure and balloon procedure using the technique of FIG. 12, guidewire 12 and catheter 38 may be removed from blood vessel 60.

Figure 13:
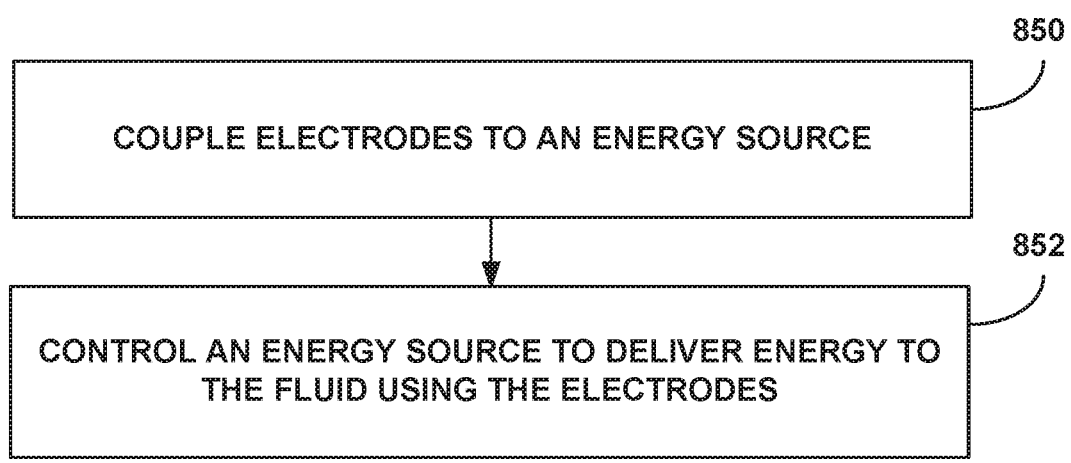
FIG. 13 is a flow diagram of an example technique of a guidewire executing cavitation.

FIG. 13 is a flow diagram of an example technique of using a guidewire to deliver cavitation energy. For illustrative purposes, the techniques of FIG. 13 are described with reference to the various aspects of guidewire 12, though such descriptions are not intended to be limiting and the techniques of FIG. 13 may be used with other guidewires or guidewires 12, and guidewires 12 may be used in other applications. The technique of FIG. 13 includes electrically coupling electrodes 30 at distal portion 22 of guidewire 12 to energy source 14 (850). Energy source 14 and guidewire 12 may be configured such that cavitation energy may be delivered via a subset of electrodes 30. For example, as described herein, guidewire 12 may include a plurality of electrodes 30 at a plurality of radial and longitudinal locations along distal portion 22 of guidewire 12. Some of electrodes 30 may define a relatively larger or smaller surface area that is configured to be exposed to fluid of the vasculature of a patient. Processing circuitry 804 is configured to select specific subsets of electrodes 30 to deliver cavitation energy in order to "steer" cavitation bubbles and therein cavitate pulse waves (e.g., bubbles 134 and pulse waves 136 of FIG. 2D). For example, energy source 14 may include switching circuitry to couple various subsets of electrodes 30 to electrical signal generator 806. Alternatively, or additionally, guidewire 12 may include more than two conductors that each are configured to couple different subsets of electrodes 30 to energy source 14.

Processing circuitry 804 may, for example, be configured to receive user input providing information regarding lesion 64 to be treated. The information may include, for example, a length and circumferential position of lesion 64. Processing circuitry 804 may then be configured to automatically determine the particular subset of electrodes 30 with which to deliver cavitation energy and the timing of the delivery of such cavitation energy. For example, processing circuitry 804 may determine that distal tip 26 is at the distal end of lesion 64 or just distal to the distal end of lesion 64 and select the one or more subsets of electrodes 30 with which to deliver the cavitation energy based on the user-provided length of lesion 64. Processing circuitry 804 may, for example, select the one or more subsets of electrodes 30 that would provide the cavitation energy along only part of the length of lesion 64, along the full length of lesion 64, or along more than the full length of lesion 64. If electrodes 30 do not span a length of guidewire 12 sufficient to cover the full length of lesion 64, then processing circuitry 804 may instruct a user (e.g., via a display and/or audio instructions provided via an audio device) to a move guidewire 12 a particular distance (e.g., corresponding to visible markers near hub 32 of guidewire 12) and then subsequently deliver cavitation energy via electrodes 30 (or a subset thereof) in response to receiving user input indicating guidewire 12 was moved.

The technique of FIG. 13 also includes controlling energy source 14 to deliver an electrical signal to a fluid within blood vessel 60 of a patient using electrodes 30 to cause the fluid to undergo cavitation to generate a pressure pulse wave within fluid (852). Guidewire 12 may deliver an electrical signal to fluid via electrodes 30 in the form of a corona, an electrical arc, a spark or the like. Guidewire 12 may cause energy source 14 to deliver electrical signal in a continuous wave signal or in the form of a plurality of pulses, and may have any suitable electrical signal parameters for creating the cavitation. For example, the electrical signal may have an amplitude of about 500 volts (V) to about 5000 V (e.g., about 1500V to about 3000 V), a pulse width of about 1 microsecond (µs) to about 5 µs for arc-type cavitation or about 10 µs to about 200 µs for corona-type cavitation, and a frequency of about 0.5 Hertz (Hz) to about 1000 Hz.

While the techniques described above are described as being performed in part by processing circuitry 804 of energy source 14, in other examples, one or more other processors may perform any part of the techniques described herein alone or in addition to processing circuitry 804 of energy source 14. Thus, reference to "a processor" may refer to "one or more processors." Likewise, "one or more processors" may refer to a single processor or multiple processors in different examples.

The techniques described in this disclosure, including those attributed to energy source 14, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

Various examples have been described. These and other examples are within the scope of the following claims.

What is claimed is:

1. A guidewire comprising:
an elongated member;
a shaft extending distally from the elongated member, wherein the elongated member and the shaft are configured to be navigated through vasculature of a patient;
a first conductor extending around the shaft to define an outer perimeter of the guidewire and configured to be electrically connected to an energy source;
a first electrode located adjacent the shaft where the first conductor extends around the shaft, wherein the first electrode is configured to be electrically coupled to the energy source via the first conductor;
a second electrode; and
a second conductor configured to electrically couple the second electrode to the energy source,
wherein the first and second electrodes are configured to deliver an electrical signal to a fluid in contact with the first and second electrodes to cause the fluid to undergo cavitation to generate a pressure pulse wave within the fluid.

2. The guidewire of claim 1, wherein the first conductor comprises an electrically conductive material at least partially covered with an electrically insulative material, and wherein the electrically insulative material defines an aperture that exposes the electrically conductive material to define the first electrode.

3. The guidewire of claim 2, wherein the first electrode is one of a first plurality of electrodes that are each defined by one of a first plurality of apertures through the electrically insulative material that exposes the electrically conductive material of the first conductor, wherein the aperture is one of the plurality of apertures.

4. The guidewire of claim 3, wherein electrodes of the first plurality of electrodes are defined by apertures of the first plurality of apertures at a plurality of longitudinal locations and a plurality of radial locations along the shaft.

5. The guidewire of claim 1, wherein the first electrode is a discrete component electrically coupled to the first conductor adjacent the shaft where the first conductor coils around the shaft.

6. The guidewire of claim 1, wherein proximal portions of the first conductor and the second conductor are embedded within the elongated member.

7. The guidewire of claim 1, wherein an outer surface of the elongated member defines a recess configured to receive at least part of the first conductor and the second conductor.

8. The guidewire of claim 7, wherein the recess defines a helix as the recess extends along a length of the elongated member.

9. The guidewire of claim 8, wherein a pitch of the helix decreases towards a distal end of the elongated member.

10. The guidewire of claim 1, wherein the first and second conductors each extend around the shaft to define a respective coil, the coils defined by the first and second conductors having substantially equal pitches and inner diameters.

11. The guidewire of claim 1, wherein the first and second conductors each comprise an electrically conductive material at least partially covered with an electrically insulative material, the electrically insulative material of the first conductor defining a first aperture that exposes the electrically conductive material of the first conductor to define the first electrode, and the electrically insulative material of the second conductor defining a second aperture that exposes the electrically conductive material of the second conductor to define the second electrode.

12. The guidewire of claim 11, wherein:
the first electrode is one of a first plurality of electrodes that are each defined by one of a first plurality of apertures through the electrically insulative material of the first conductor that exposes the electrically conductive material of the first conductor; and
the second electrode is one of a second plurality of electrodes that are each defined by one of a second plurality of apertures through the electrically insulative material that exposes the electrically conductive material of the second conductor.

13. The guidewire of claim 12, wherein:
electrodes of the first plurality of electrodes are defined by apertures of the first plurality of apertures at a plurality of longitudinal locations and a plurality of circumferential locations along the shaft; and
electrodes of the second plurality of electrodes are defined by apertures of the second plurality of apertures at a plurality of longitudinal locations and a plurality of radial locations along the shaft.

14. The guidewire of claim 1, wherein the second conductor comprises an electrically conductive core of the elongated member and the first conductor is embedded within the elongated member.

15. The guidewire of claim 14, wherein the elongated member includes at least one electrically insulative layer that electrically insulates the first conductor from the electrically conductive core of the second conductor.

16. The guidewire of claim 14, wherein the shaft includes the second electrode.

17. The guidewire of claim 1, wherein the first conductor extends around the shaft to define a first coil, the guidewire further comprising one or more spacing filars that each extend between turns of the first coil around the shaft to define a respective spacing coil, the first coil and the one or more spacing coils having substantially equal pitches and inner diameters.

18. The guidewire of claim 17, wherein the one or more spacing filars include at least three spacing filars.

19. The guidewire of claim 1, further comprising a radiopaque distal tip that is distal to the shaft.

20. The guidewire of claim 1, wherein the elongated member does not define a lumen that extends to a distal tip of the guidewire.

21. The guidewire of claim 1, wherein the elongated member defines an outer diameter of about 0.25 millimeters and 0.75 millimeters.

22. The guidewire of claim 1, wherein the guidewire defines a longitudinal length of a distal portion of about 10 millimeters to about 30 millimeters.

23. The guidewire of claim 1, wherein the elongated member decreases in stiffness in a distal direction.

24. The guidewire of claim 1, wherein the elongated member includes a hypotube.

25. The guidewire of claim 1, wherein the shaft is a solid shaft.

26. A method comprising:
introducing a guidewire through vasculature of a patient to a target treatment site, the guidewire comprising:
- an elongated member;
- a shaft extending distally from the elongated member wherein the elongated member and the shaft are configured to be navigated through vasculature of the patient;
- a first conductor extending around the shaft to define an outer perimeter of the guidewire and configured to be electrically connected to an energy source;
- a first electrode located adjacent the shaft where the first conductor extends around the shaft, wherein the first electrode is configured to be electrically coupled to the energy source via the first conductor;
- a second electrode; and
- a second conductor configured to electrically couple the second electrode to the energy source; and controlling an energy source to deliver an electrical signal to a fluid in contact with the first and second electrode to cause the fluid to undergo cavitation and generate a pressure pulse wave within the fluid.

27. The method of claim 26, wherein the electrical signal is a first electrical signal, the method further comprising:
- after delivering the first electrical signal, repositioning the guidewire within the vasculature; and
- after repositioning the guidewire within the vasculature, delivering a second electrical signal to cause the fluid to undergo further cavitation and generate further pressure pulse waves within the fluid.

28. The method of claim 26, the method further comprising:
- navigating a distal portion of a catheter over the guidewire using a guidewire lumen of the catheter in response delivering the electrical signal to the fluid in contact with the first and second electrode; and
- deploying a medical device at the target treatment site from the distal portion of the catheter.

* * * * *